US012708414B2

(12) United States Patent
Dacosta et al.

(10) Patent No.: US 12,708,414 B2
(45) Date of Patent: Aug. 18, 2026

(54) BONE PLATE HOLE CAPS, BONE PLATE SYSTEMS, AND METHODS USING SAME

(71) Applicant: Paragon 28, Inc., Englewood, CO (US)

(72) Inventors: Albert Dacosta, Lone Tree, CO (US); Richard David Hunt, Arvada, CO (US); Spanky Raymond, Uniontown, OH (US); Kyle James Hartson, Denver, CO (US); Shane Miller, Dublin (IE)

(73) Assignee: Paragon 28, Inc., Englewood, CO (US)

( * ) Notice: Subject to any disclaimer, the term of this patent is extended or adjusted under 35 U.S.C. 154(b) by 743 days.

(21) Appl. No.: 17/819,492

(22) Filed: Aug. 12, 2022

(65) Prior Publication Data

US 2022/0387085 A1 Dec. 8, 2022

Related U.S. Application Data

(63) Continuation of application No. PCT/US2021/017888, filed on Feb. 12, 2021.

(Continued)

(51) Int. Cl.
*A61B 17/80* (2006.01)

(52) U.S. Cl.
CPC ...... *A61B 17/8004* (2013.01); *A61B 17/8057* (2013.01)

(58) Field of Classification Search
CPC . A61B 17/80; A61B 17/8004; A61B 17/8052; A61B 70/80; A61B 70/8004
See application file for complete search history.

(56) References Cited

U.S. PATENT DOCUMENTS 5,607,426 A * 3/1997 Ralph ........................ A61F 2/34 606/287
6,139,550 A * 10/2000 Michelson ............. A61B 17/80 606/295

(Continued)

FOREIGN PATENT DOCUMENTS

JP 2013521095 A 6/2013
JP 2019533564 A 11/2019

(Continued)

OTHER PUBLICATIONS

International Search Report and Written Opinion of the International Searching Authority for International Application No. PCT/US2021/017888 mailed on Apr. 23, 2021, 9 pages.

(Continued)

*Primary Examiner* — Christina C Lauer
(74) *Attorney, Agent, or Firm* — Heslin Rothenberg Farley & Mesiti P.C.

(57) ABSTRACT

A bone plate system includes, for example, a bone plate and at least one bone plate hole cap. The bone plate includes a body having a first surface, a bone-engaging surface, and a plurality of through-openings. The bone plate hole cap includes a body having a first surface, a second surface, and a peripheral surface. The bone plate hole cap is securable in at least one of the through-openings in the bone plate. When the bone plate hole cap is secured in the through opening, the second surface of the bone plate hole cap is disposed adjacent to the bone-engaging surface of the bone plate. The bone plate with the bone plate hole cap secured in the through-hole increases the bending strength of a portion of the bone plate across the bone plate hole cap compared to the portion of the bone plate without the bone plate hole cap.

24 Claims, 18 Drawing Sheets

Related U.S. Application Data

(60) Provisional application No. 62/976,662, filed on Feb. 14, 2020.

(56) References Cited

U.S. PATENT DOCUMENTS

| | | | |
|---|---|---|---|
| 6,527,776 B1 | 3/2003 | Michelson | |
| 8,172,886 B2 | 5/2012 | Castaneda et al. | |
| 2005/0010225 A1 | 1/2005 | Del Medico | |
| 2007/0260244 A1 | 11/2007 | Wolter | |
| 2009/0287215 A1 | 11/2009 | Fisher et al. | |
| 2012/0053637 A1 | 3/2012 | Imwinkelried et al. | |
| 2012/0059425 A1* | 3/2012 | Biedermann | A61B 17/8877 606/291 |
| 2014/0107710 A1* | 4/2014 | Forderer | A61B 17/842 606/281 |
| 2015/0289914 A1 | 10/2015 | Forderer et al. | |
| 2016/0296319 A1 | 10/2016 | Lopez | |
| 2016/0324547 A1 | 11/2016 | Miller et al. | |
| 2018/0110507 A1 | 4/2018 | Tordi et al. | |
| 2018/0256228 A1 | 9/2018 | Biedermann | |

FOREIGN PATENT DOCUMENTS

| | | |
|---|---|---|
| WO | 2006102110 | 9/2006 |
| WO | 2011110916 A1 | 9/2011 |
| WO | 2013103474 A1 | 7/2013 |
| WO | 2018080866 A1 | 5/2018 |
| WO | 2021163511 A1 | 8/2021 |

OTHER PUBLICATIONS

International Preliminary Report on Patentability for International Application No. PCT/US2021/017888 dated Aug. 11, 2022, 8 pages, International Bureau of WIPO.

DaCosta et al., European Extended Search Report for International Application No. PCT/US2021/017888 (publised as WO 2021/163511), mailed on Feb. 21, 2024, 11 pages. Feb. 21, 2024.

DaCosta et al., Japanese Office Action for Japanese Patent Application No. 2022-549076 (based on International Application No. PCT/US2021/017888, published as WO 2021/163511), mailed on Aug. 27, 2024, 6 pages. Aug. 27, 2024.

DaCosta et al., Japanese Office Action for Japanese Patent Application No. 2022-549076 (based on International Application No. PCT/US2021/017888, published as WO 2021/163511), mailed on Apr. 30, 2025, 8 pages, Apr. 30, 2025.

DaCosta et al., European Office Action for European Patent Application No. 21753735.6 (based on International Application No. PCT/US2021/017888, published as WO 2021/163511), mailed on Feb. 17, 2025, 11 pages, Feb. 17, 2025.

DaCosta et al., Brazilian Office Action for Brazilian Patent Application No. BR1120220161522 (based on International Application No. PCT/US2021/017888, published as WO 2021/163511), mailed on Mar. 13, 2025, 10 pages, Mar. 13, 2025.

DaCosta et al., Brazilian Office Action for Brazilian Patent Application No. BR1120220161522 (based on International Application No. PCT/US2021/017888, published as WO 2021/163511), mailed on Aug. 28, 2024, 8 pages, Aug. 28, 2024.

* cited by examiner

PROVIDING A BONE PLATE HAVING A FIRST SURFACE, A SECOND SURFACE, AND A PLURALITY OF THROUGH-OPENINGS EXTENDING FROM THE FIRST SURFACE TO THE SECOND SURFACE — 1100

PROVIDING A BONE PLATE HOLE CAP HAVING A FIRST SURFACE, A SECOND SURFACE, AND A PERIPHERAL SURFACE EXTENDING BETWEEN THE FIRST SURFACE AND THE SECOND SURFACE OF THE BONE PLATE HOLE CAP — 1200

SELECTIVELY SECURING THE BONE PLATE HOLE CAP IN ONE OF THE PLURALITY OF THROUGH-OPENINGS IN THE BONE PLATE — 1300

ACCESSING A BONE — 1400

SELECTIVELY POSITIONING THE BONE PLATE WITH THE BONE PLATE HOLE CAP ADJACENT TO AN OUTER SURFACE OF THE BONE WITH THE BONE PLATE HOLE CAP DISPOSED OVER A JOINT LINE — 1500

SECURING THE BONE PLATE TO THE BONE WITH A PLURALITY OF FIXATION ELEMENTS EXTENDING THROUGH SOME OF THE OTHER PLURALITY OF THROUGH-OPENINGS IN THE BONE PLATE, WHEREIN THE BONE PLATE WITH THE AT LEAST ONE BONE PLATE HOLE CAP IN THE ONE OF THE PLURALITY OF THROUGH-HOLES INCREASES THE BENDING STRENGTH OF THE SECURED BONE PLATE ADJACENT TO THE JOINT LINE COMPARED TO THE SECURED BONE PLATE ADJACENT TO THE JOINT LINE WITHOUT THE BONE PLATE HOLE CAP — 1600

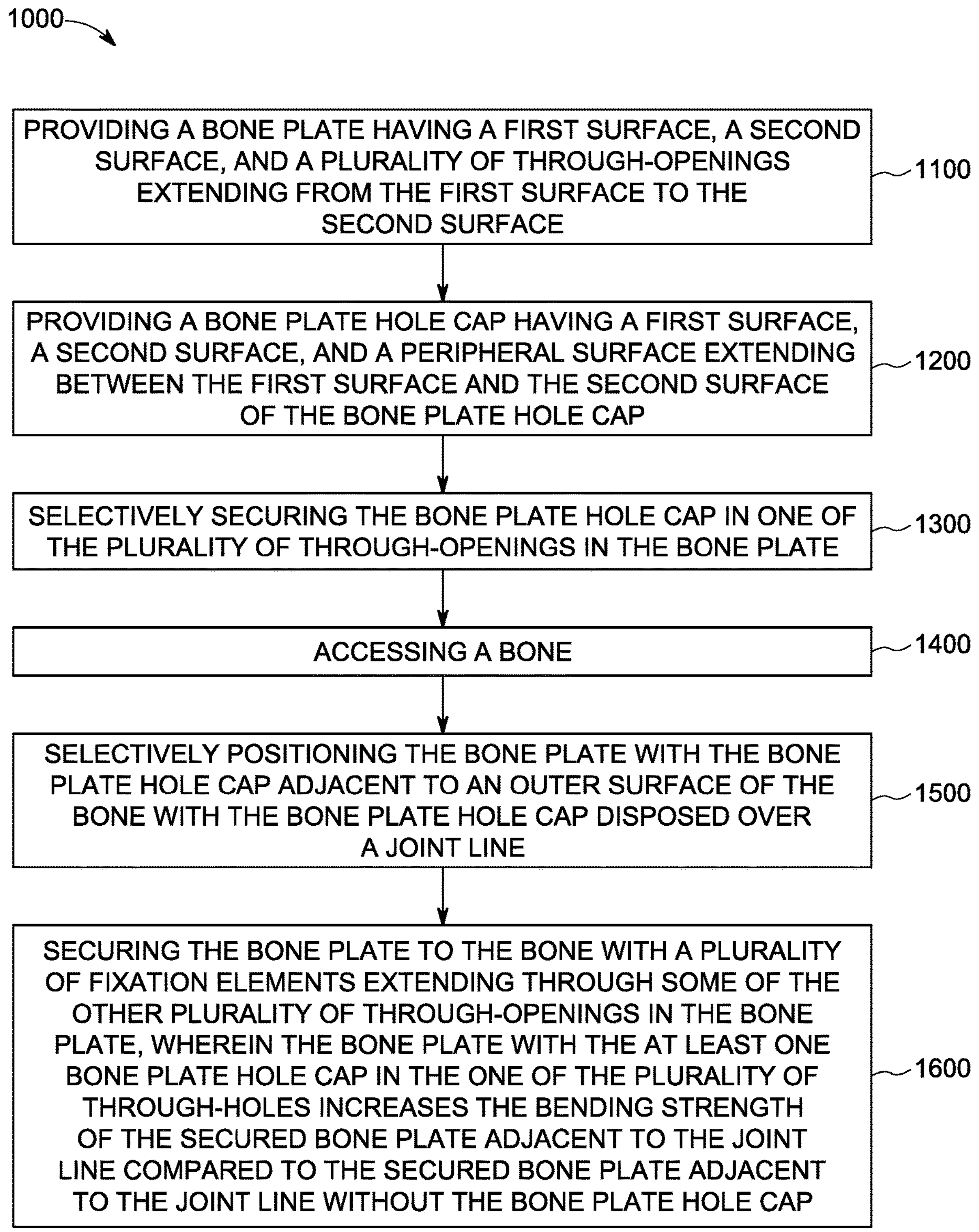

FIG. 30

BONE PLATE HOLE CAPS, BONE PLATE SYSTEMS, AND METHODS USING SAME

CROSS REFERENCE TO RELATED APPLICATION

This application is a Bypass Continuation application to PCT International Application No. PCT/US2021/017888, filed Feb. 12, 2021, and entitled "Bone Plate Hole Caps, Bone Plate Systems, and Methods Using Same," which claims priority benefit under 35 U.S.C. § 119(e) of U.S. Provisional Patent Application No. 62/976,662, filed Feb. 14, 2020, and entitled "Bone Plate Hole Caps, Bone Plate Systems, and Methods Using Same," the disclosures of each of these applications are hereby incorporated herein by reference in their entirety.

TECHNICAL FIELD

The present disclosure relates generally to repair of bones such as fractured or broken bones, or for correcting bone deformities such as in the foot and ankle.

BACKGROUND

Bone plates are used in orthopedics for the fixation of bone segments, for example, after fractures. Typically, bone plates are metal bars or plates with perforations for the insertion of screws and are used to immobilize fractured segments and/or correct deformities.

Locking elements have been employed to lock the heads of the screws to the bone plates to prevent screw backout. For example, a locking element is attached to the bone plate to engage the top of the installed screw so that installed screw is prevented from movement.

SUMMARY

Aspects of the present disclosure provide for repair of bones such as fractured or broken bones, or for correcting bone deformities such as in the foot and ankle.

Shortcomings of the prior art are overcome and additional advantages are provided through the provision in one embodiment of a bone plate system, which includes, for example, a bone plate and at least one bone plate hole cap. The bone plate includes a body having a first surface, a bone-engaging surface, and a plurality of through-openings extending from the first surface to the bone-engaging surface. The plurality of through-openings define an inner surface extending between the first surface to the bone-engaging surface of the bone plate. The at least one bone plate hole cap includes a body having a first surface, a second surface, and a peripheral surface disposed between the first surface and the second surface of the at least one bone plate hole cap. The at least one bone plate hole cap is securable in at least one of the plurality of through-openings in the bone plate. When the bone plate hole cap is secured in the at least one of the plurality of through-openings, the second surface of the bone plate hole cap is disposed adjacent to the bone-engaging surface of the bone plate. The bone plate with the at least one bone plate hole cap secured in the one of the plurality of through-openings increases the bending strength of a portion of the bone plate across the bone plate hole cap compared to the portion of the bone plate without the bone plate hole cap.

In another embodiment, a surgical method includes, for example, providing a bone plate having a first surface, a second surface, and a plurality of through-openings extending from the first surface to the second surface, providing a bone plate hole cap having a first surface, a second surface, and a peripheral surface extending between the first surface and the second surface of the bone plate hole cap, selectively securing the bone plate hole cap in one of the plurality of through-openings in the bone plate, accessing a bone, selectively positioning the bone plate with the bone plate hole cap adjacent to an outer surface of the bone with the bone plate hole cap disposed over a joint line, and securing the bone plate to the bone with a plurality of fixation elements extending through at least some of the other plurality of through-openings in the bone plate. The bone plate with the at least one bone plate hole cap in the one of the plurality of through-openings increases the bending strength of the secured bone plate disposed adjacent to the joint line compared to the secured bone plate adjacent to the joint line without the bone plate hole cap These and other objects, features and advantages of the present disclosure will become apparent from the following detailed description of the various embodiments of the present disclosure taken in conjunction with the accompanying drawings.

BRIEF DESCRIPTION OF THE DRAWINGS

The accompanying drawings, which are incorporated in and constitute a part of the specification, illustrate embodiments of the present disclosure and together with the detailed description herein, serve to explain the principles of the present disclosure. The drawings are only for purposes of illustrating preferred embodiments and are not to be construed as limiting the present disclosure. It is emphasized that, in accordance with the standard practice in the industry, various features are not drawn to scale. In fact, the dimensions of the various features may be arbitrarily increased or reduced for clarity of discussion. The foregoing and other objects, features and advantages of the disclosure are apparent from the following detailed description taken in conjunction with the accompanying drawings in which:

FIG. 30 is a flowchart of a surgical method employing a bone plate system having a bone plate hole cap, according to an embodiment of the present disclosure;

DETAILED DESCRIPTION

Figure 1:
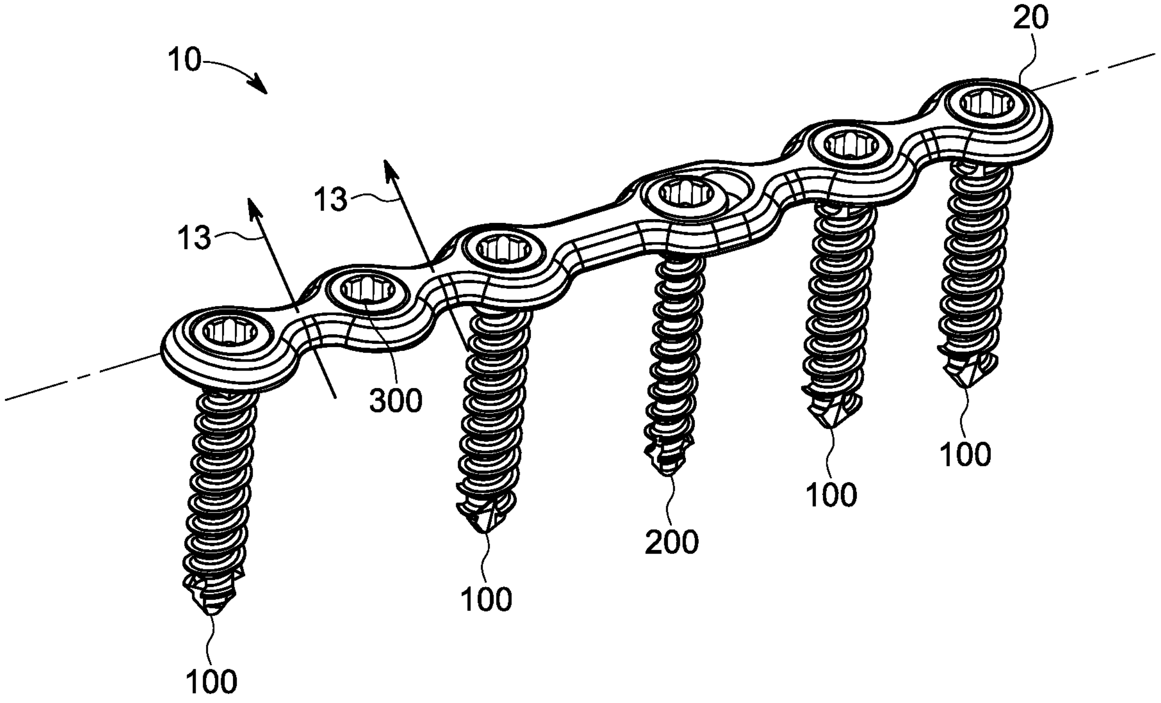
FIG. 1 is a top perspective view of a bone plate system, according to an embodiment of the present disclosure.

Generally stated, disclosed herein are bone plate hole caps, bone plate systems, and methods for repair of bones such as fractured or broken bones, or for correcting bone deformities such as in the foot and ankle. It will be appreciated that the bone plate hole caps, bone plate systems, and methods are also applicable to other types of repair of bones.

In this detailed description and the following claims, the words proximal, distal, anterior or plantar, posterior or dorsal, medial, lateral, superior and inferior are defined by their standard usage for indicating a particular part or portion of a bone, joint (or any other anatomical structure) or implant according to the relative disposition of the natural bone, joint (or any other anatomical structure) or directional terms of reference. For example, “proximal” means the portion of a device or instrument nearest the torso, while “distal” indicates the portion of the device or instrument farthest from the torso. As for directional terms, “anterior” is a direction towards the front side of the body, “posterior” means a direction towards the back side of the body, “medial” means towards the midline of the body, “lateral” is a direction towards the sides or away from the midline of the body, “superior” means a direction above and “inferior” means a direction below another object or structure. Further, specifically in regards to the foot and/or ankle, the term “dorsal” refers to the top of the foot and the term “plantar” refers the bottom of the foot.

Similarly, positions or directions may be used herein with reference to anatomical structures or surfaces. For example, as the current instruments, guides, systems and related methods (and components thereof) are described herein with reference to use with the bones of the ankle, the bones of the foot, ankle and lower leg may be used to describe the surfaces, positions, directions or orientations of the instruments, guides, systems and related methods (and components thereof). Further, the instruments, guides, systems and related methods, and the aspects, components, features and the like thereof, disclosed herein may be described with respect to one side of the body (e.g., the left or right ankle) for brevity purposes. However, as the human body is relatively symmetrical or mirrored about a line of symmetry (midline), it is hereby expressly contemplated that the instruments, guides, systems and related methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the instruments, guides, systems and related methods, and the aspects, components, features and the like thereof, described herein with respect to the right ankle of a patient may be mirrored so that they likewise function with the left ankle of the patient. Further, the instruments, guides, systems and related methods, and the aspects, components, features and the like thereof, disclosed herein are described with respect to the ankle for brevity purposes, but it should be understood that the instruments, guides, systems and related methods (and components thereof) may be used with other joints of a human body (or other mammalian body).

Figure 2:
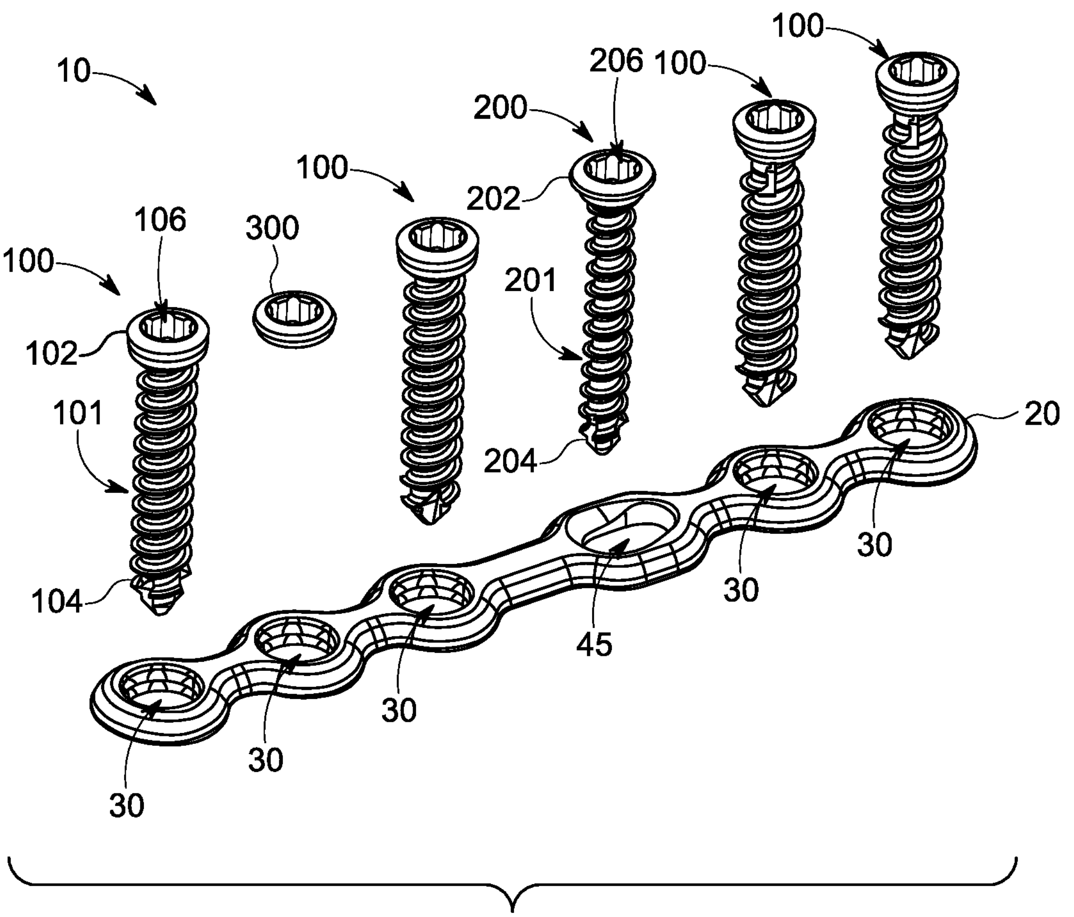
FIG. 2 is an exploded, top perspective view of the bone plate system of FIG. 1, according to an embodiment of the present disclosure.
Figure 3:
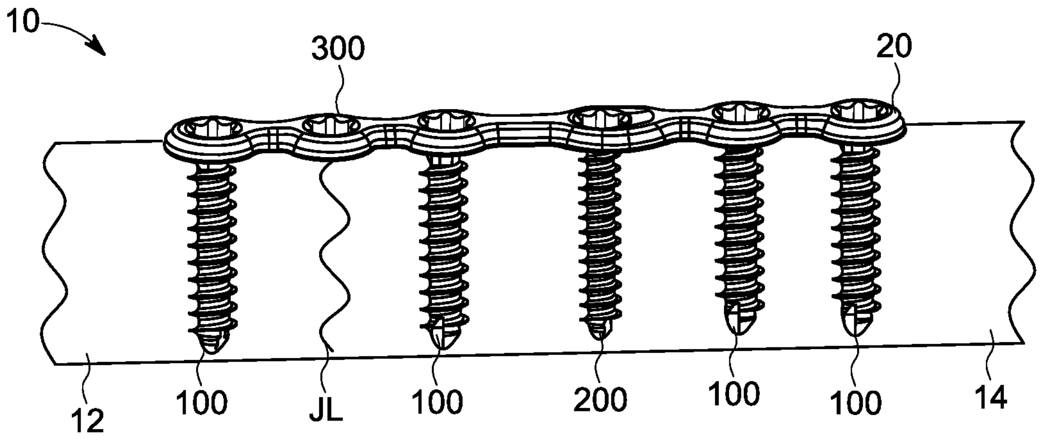
FIG. 3 is a side perspective view of the bone plate system of FIG. 1, according to an embodiment of the present disclosure.

FIGS. 1-3 illustrate a bone plate system 10, according to an embodiment of the present disclosure. For example, the bone plate system 10 may include a bone plate 20, a plurality of fixation elements 100 and 200, and at least one bone plate hole cap 300. From the present description, it will be appreciated that the combination of the bone plate 20 with the bone plate hole cap 300 may provide additional strength to the bone plate 20, particularly when a fixation element is not installed in the corresponding through-opening 30 (FIG. 2).

With reference to FIG. 3, the bone plate system 10 may be operable for attachment to a first bone or portion 12 and a second bone or portion 14. The combination of the bone plate 20 and the bone plate hole cap 300 may provide additional strength to the bone plate 20 over areas such as a joint line JL in the bone. For example, a bone plate through-opening without a screw inserted is inherently weak at that location in bending. By filling the through-opening with a structural member or bone plate hole cap, the bending strength of the bone plate with the bone plate hole cap may be improved or strengthened compared to the through-opening in the bone plate remaining empty. As described further below, the configuration of the bone plate hole caps may provide for an additional fulcrum or tensioner of tendons. In some embodiments, the configuration of the bone plate hole cap may provide an eyelet for soft tissue fixation or "pulley fulcrum" for soft tissue tape and prescribed direction of pull/vector.

Figure 4:
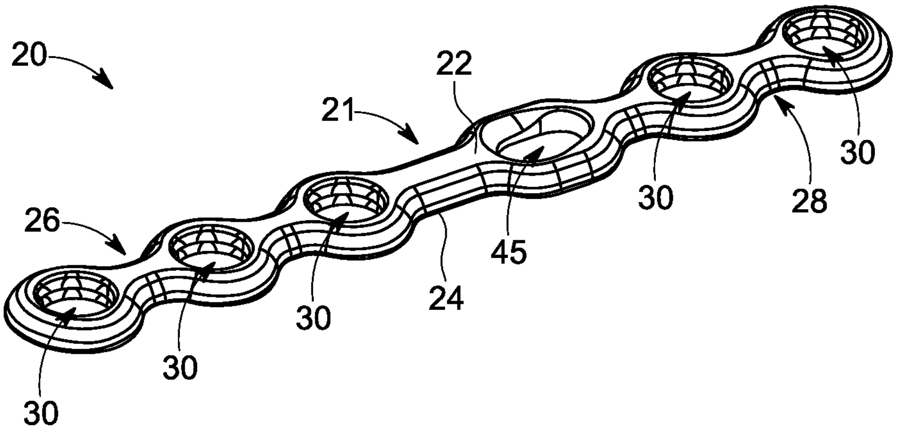
FIG. 4 is a top perspective view of the bone plate of FIG. 1, according to an embodiment of the present disclosure.
Figure 5:
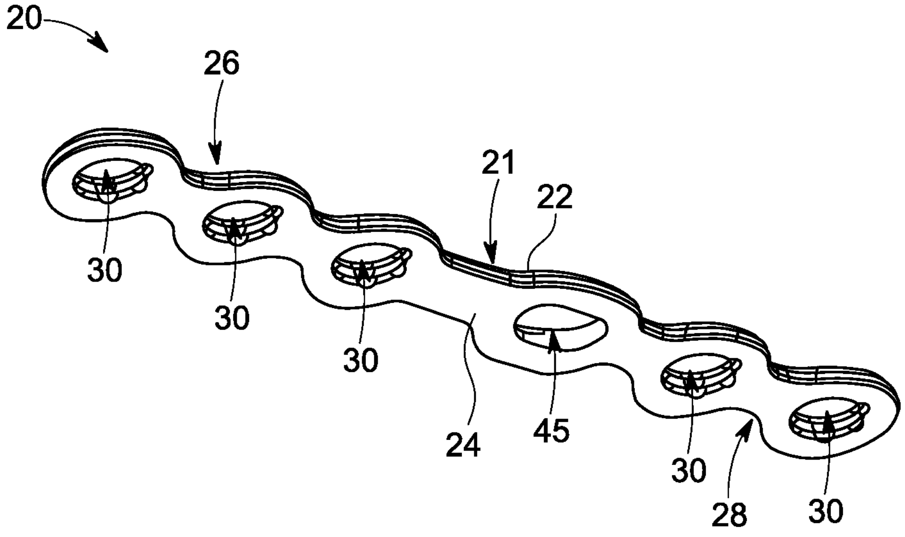
FIG. 5 is a bottom perspective view of the bone plate of FIG. 1, according to an embodiment of the present disclosure.

With reference to FIGS. 4 and 5, the bone plate 20 may include a body 21 having a first surface 22 and a second surface 24 such as a bone-engaging surface. A first end portion 26 is operable for attachment to the first bone portion 12 (FIG. 3) and a second end portion 28 is operable for attachment to the second bone 14 (FIG. 3). The bone plate 20 may also include one or more through-openings 30 extending from the first surface 22 to the second surface 24 of the bone plate 20. The bone plate 20 may include one or more through-opening 45 such as a compression slot extending from the first surface 26 to the second surface 28 of the bone plate 20. The through-openings 30 may be threaded through-holes, and may be similarly configured. The through-opening 30 may be used to insert fixation elements, for example, the bone screws 100 (FIG. 3) into the first bone 12 (FIG. 3), for example, the distal bone, and into the second bone 14 (FIG. 3), for example, the proximal bone. The at least one through-opening 30 may be used to insert a fixation element, for example, the bone screws 100 into the second bone 14 (FIG. 3), for example, the proximal bone. The compression slot 45 may allow for insertion of a fixation element 200, which may translate within the compression slot 45 while the distal and proximal bones 12 and 12 (FIG. 3) are moved or compressed.

Figure 6:
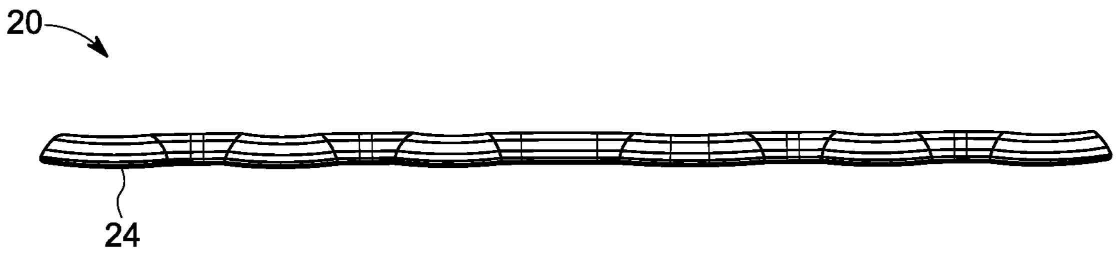
FIG. 6 is a side elevational view of the bone plate of FIG. 1, according to an embodiment of the present disclosure.
Figure 7:
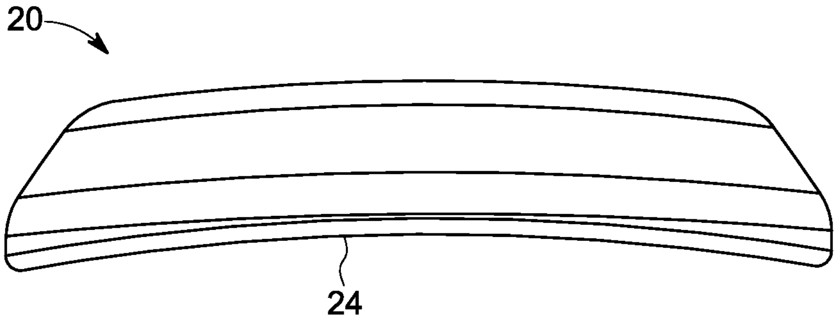
FIG. 7 is an enlarged end view of the bone plate of FIG. 1, according to an embodiment of the present disclosure.

As shown in FIGS. 6 and 7, the bone plate 20 may have a curved second surface 24 that extends along the length of the bone plate 20. For example, the bottom surface 24 may be configured to conform to the natural shape of the bone cortex or bone portions to which it is to be attached. In other embodiments, the second surface of the bone plate may be flat or planar. The bone plate 20 may be made from, for example, a biocompatible material, including but not limited to a metal such as titanium, stainless steel, cobalt chromium, a polymer, a composite, etc.

With reference again to FIG. 2, the bone screws 100 may include an elongate body 101 having a proximal portion 102 and a distal portion 104. The proximal portion 102 may have a diameter sized larger than the diameter of the distal portion 102. For example, the distal portion 104 may have a diameter sized to pass through the through-openings 30 in the bone plate 20. The proximal portion 102 may have a diameter sized to mate and engage the through-openings 30 in bone plate 20. The proximal portion 102 may be a threaded distal portion, for example, threaded to mate and engage the threaded through-openings 30 in the bone plate 20 to secure the base plate 20 to the patient's bone. The distal portion 104 may be a threaded distal portion, for example, threaded to engage a patient's bone to secure the base plate 20 to the patient's bone. The distal portion 104 may be, for example, configured or sized and shaped to conserve bone. In some embodiments, the threaded distal portion 104 may have, for example, a texture or coating to provide for porous fixation. The proximal portion 102 may have, for example, a recess or drive feature 106 for engagement with a tool such as a hex driver for inserting or removing the bone screw 100.

The bone screw 200 may include an elongate body 201 having a proximal portion 202 and a distal portion 204. The proximal portion 202 may have a diameter sized larger than the diameter of the distal portion 204. For example, the distal portion 204 may have a diameter sized to pass through the through-opening or compression slot 45 in the bone plate 20. The proximal portion 202 may have a diameter sized to mate and engage the compression slot 45 in the bone plate 20. The proximal portion 202 may have frustoconical configuration and is sized to mate and engage portions of the compression slot 45 of bone plate 20. The distal portion 204 may be a threaded distal portion, for example, threaded to engage the patient's bone to secure the bone plate 20 to the patient's bone. The distal portion 204 may be, for example, configured or sized and shaped to conserve bone. In some embodiments, the threaded distal portion 204 may have, for example, a texture or coating to provide for porous fixation. The proximal portion 202 of bone screw 200 may have, for example, a recess or drive feature 206 for engagement with a tool such as a hex driver for inserting or removing the bone screw 200. The bone screws 100 and 200 may be made from, for example, a biocompatible material, including but not limited to a metal such as titanium, stainless steel, cobalt chromium, or other suitable material.

FIGS. 8-12 illustrates the bone plate hole cap 300, which may include a body 301 having a first surface 322 and a second surface 324, and a peripheral surface 326 disposed between the first surface 322 and the second surface 324 of the bone plate hole cap 300. The peripheral surface 326 may be sized to be restrained or secured in one of the through-openings 30 (FIG. 2) in the bone plate 20 (FIG. 2). The peripheral surface 326 may be sized to mate and engage the through-openings 30 in the bone plate 20. For example, the peripheral surface 326 may be a threaded peripheral surface to mate and engage the threaded through-openings 30 in the bone plate 20. The bone plate hole cap 300 may include a through-opening 330 extending from the first surface 322 of the body 301 of the bone plate hole cap 300 to the second surface 324 of the body 301 of the bone plate hole cap 300. The through-opening 330 of the body 301 may have, for example, a drive feature for engagement with a tool such as a hex drive for inserting or removing the bone plate hole cap 300 from the bone plate 20 (FIG. 2). For example, with reference to FIG. 11, the bone plate hole cap 300 may be formed from a solid blank disk. The through-opening 330 in body 301 may be formed by drilling six holes having a diameter D1, and then drilling a hole in the center of the disk having a diameter D2.

Figure 13:
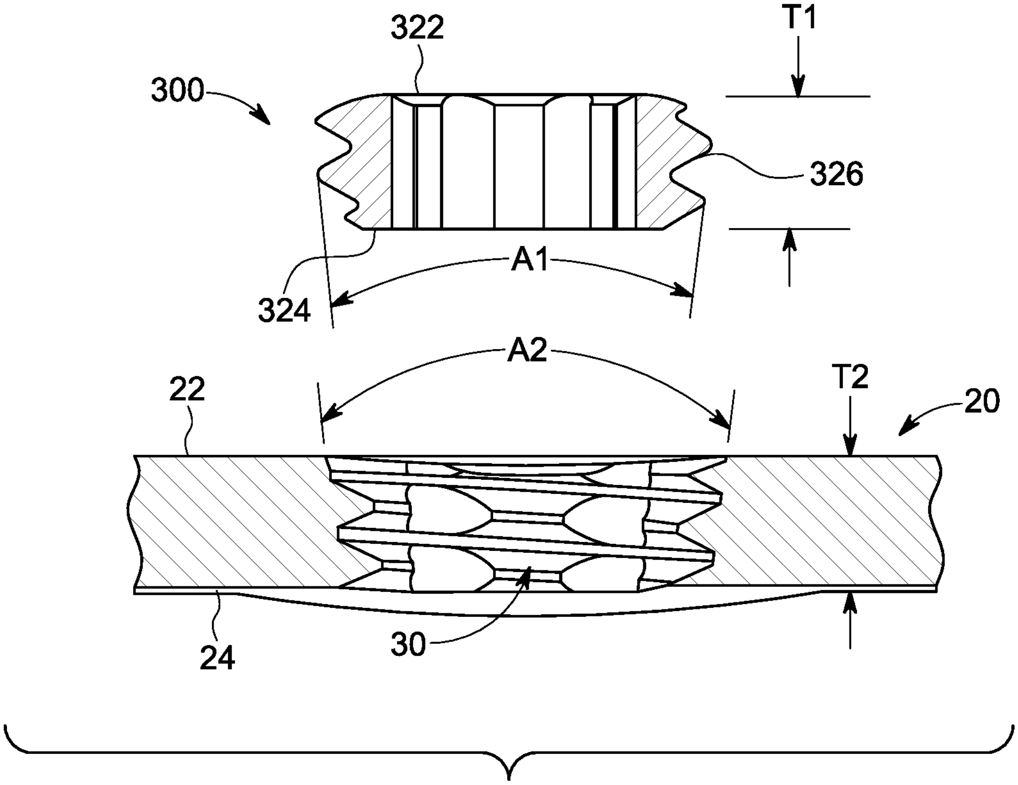
FIG. 13 is an enlarged, exploded cross-sectional view taken along line 13-13 in FIG. 1 of the bone plate and bone plate hole cap, according to an embodiment of the present disclosure.
Figure 14:
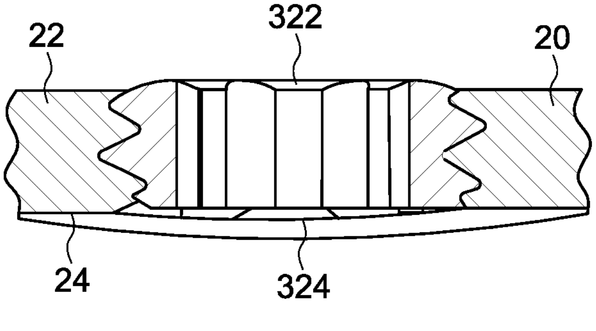
FIG. 14 is an enlarged cross-sectional view taken along line 13-13 in FIG. 1 of the bone plate and bone plate hole cap, according to an embodiment of the present disclosure.

With reference to FIGS. 13 and 14, in some embodiments, the bone plate hole cap 300 may be secured and/or locked in at least one of the plurality of the through-openings 30 (FIG. 13) in the bone plate 20. For example, the through-opening 30 (FIG. 13) in the bone plate 20 may include a tapered configuration from the first surface 22 to the second surface 24 of the bone plate 20. The peripheral surface 326 (FIG. 13) of the bone plate hole cap 300 may include a mating tapered peripheral configuration from the first surface 322 to the second surface 324 of the bone plate hole cap 300. The tapered configuration of the bone plate hole cap 300 may be disposed at an angle A1 between about 2 degrees and about 10 degrees, about 4 degrees and about 8 degrees, at 6 degrees, or disposed at a suitable angle. The tapered configuration of the through-opening 30 (FIG. 13) in the bone plate 20 may be disposed at an angle A2 between about 2 degrees and about 10 degrees, about 4 degrees and about 8 degrees, at 6 degrees, or disposed at a suitable angle. The bone plate hole cap 300 may include a first thickness T1 (FIG. 13) between the first surface 322 and the second surface 324 of the bone plate hole cap 300. The bone plate 20 around the through-openings 30 may include a second thickness T2 (FIG. 13) between the first surface 22 and the second surface 24 of the bone plate 20. In some embodiments, the first thickness T1 (FIG. 13) may be the same as the second thickness T2 (FIG. 13). It will be appreciated that the other through-openings 30 (FIG. 2) of the bone plate 20 may be similarly configured, and one or more similarly configured bone plate hole caps 300 may be installed in the other through-openings.

As shown in FIG. 14, when the bone plate hole cap 300 is secured and/or locked in the through-opening 30 (FIG. 13), the second surface 324 of the bone plate hole cap 300 is disposed adjacent to the second surface 24 of the bone plate 20. In some embodiments, the first surface 322 of the bone plate hole cap may be aligned with the first surface 22 of the bone plate 20.

Figure 15:
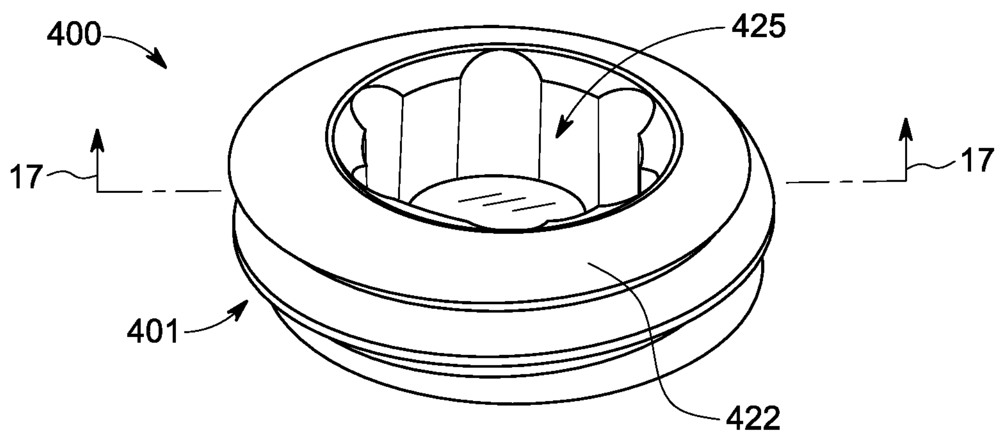
FIG. 15 is a top perspective view of another bone plate hole cap, according to an embodiment of the present disclosure.
Figure 16:
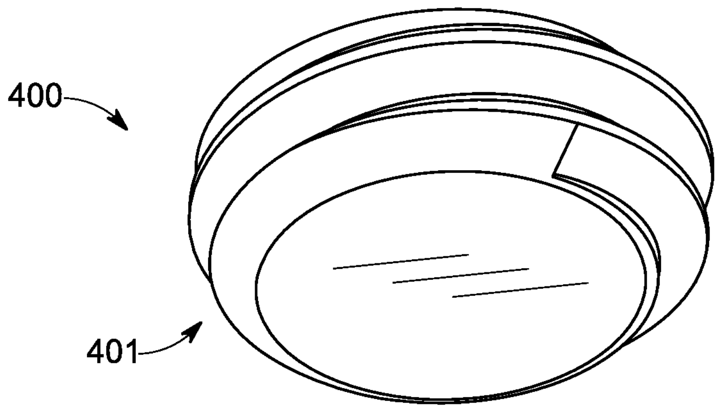
FIG. 16 is a bottom perspective view of the bone plate hole cap of FIG. 15, according to an embodiment of the present disclosure.
Figure 17:
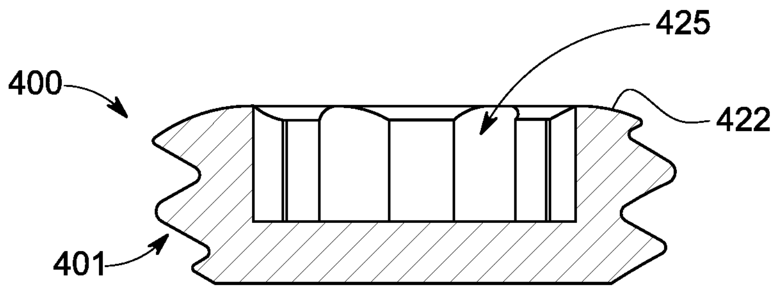
FIG. 17 is a cross-sectional view taken along line 17-17 in FIG. 15 of the bone plate hole cap, according to an embodiment of the present disclosure.

FIGS. 15-17 illustrate another embodiment of a bone plate hole cap 400, according to the present disclosure. The bone plate hole cap 400 may be essentially the same as bone plate hole cap 300 (FIGS. 8-12) with the exception that a body 401 of the bone plate hole cap 400 does not include a through-opening. For example, the body 401 may include a recess or cavity 425 that does not extend through the full thickness of the body 401.

Figure 18:
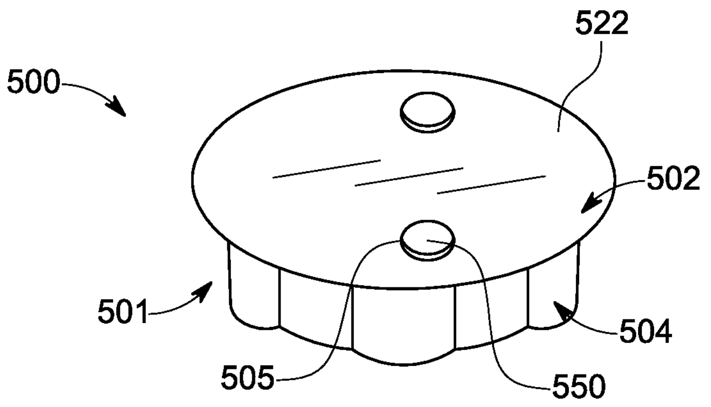
FIG. 18 is a top perspective view of a cover receivable in an opening in a bone plate hole cap, according to an embodiment of the present disclosure.

FIG. 18 illustrates a cover 500 receivable in the through-opening 330 (FIG. 8) in the bone plate hole cap 30 (FIG. 8) or the recess 425 (FIG. 15) in bone plate hole cap 400 (FIG. 15), according to an embodiment of the present disclosure. For example, the cover 500 may include a body 501 that is operable as a soft tissue button or cover. The cover 500 may include a top portion 502 and a lower portion 504 sized to be press fit into the through-opening 330 (FIG. 8) in the bone plate hole cap 30 (FIG. 8) or the recess 425 (FIG. 15) in bone plate hole cap 400 (FIG. 15). In other embodiments, the cover 500 may be attached to the bone plate hole cap in a snap-fit manner or other suitable connection. A first surface 522 of the cover 500 may be alignable with the first surface 322 (FIG. 8) of the bone plate hole cap 30 (FIG. 8) or the first surface 422 (FIG. 15) of the bone plate hole cap 400 (FIG. 15). The top portion 502 may be a solid cover or may include one or more holes 505 operable with one or more sutures 550 for attachment to soft tissue or a tendon. In other embodiments, the holes in the body of the cover may be oval, slots, or other suitable configurations. The covers may be a biopolymer material, metal, or other suitable material. The covers may be formed from a material that is softer than the material used to form the bone plate hole cap. With reference again to FIG. 8, in other embodiments, the bone plate hole cap 300 may include one or more holes or passageways 360 operable with one or more sutures (not shown) for attachment to soft tissue or a tendon. For example, the hole 360 may extend from first surface 322 to an inner surface 332 defining the through-opening 330. It will be appreciated that other holes or passageways may also be provided around the first surface allowing a surgeon to select a desired hole or passageways for use with one or more sutures.

Figure 19:
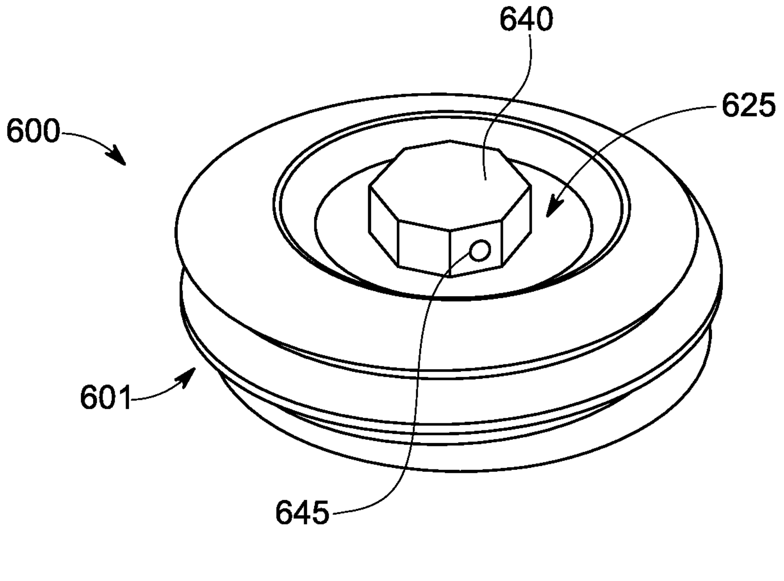
FIG. 19 is a top perspective view of another bone plate hole cap, according to an embodiment of the present disclosure.

FIG. 19 illustrates another embodiment of a bone plate hole cap 600, according to the present disclosure. The bone plate hole cap 600 may be essentially the same as bone plate hole cap 400 (FIGS. 8-12) with the exception that a body 601 of the bone plate hole cap 400 is not configured for receiving a male tool drive, but instead configured for receiving a female socket drive. For example, the body 601 may have a recess 625 having a projection 640 such as a hexagonal projection therein. The projection 640 may include a hole or passageway 645 for attachment to soft tissue or a tendon. A suitable cover (not shown) may be configured to cover the recess 625 in body 601 of bone plate hole cap 600. The cover may be a biopolymer material, metal, or other suitable material. The cover may be formed from a material that is softer than the material used to form the bone plate hole cap.

Figure 20:
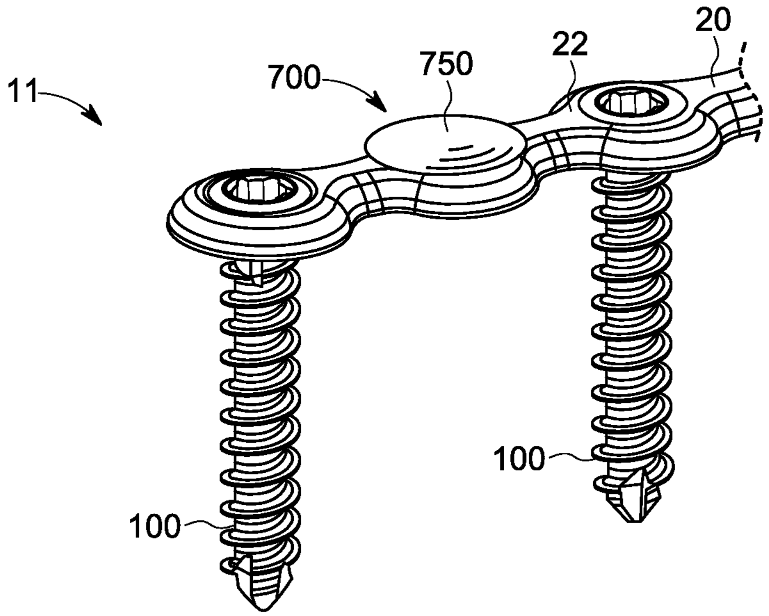
FIG. 20 is a perspective view of another bone plate system, according to an embodiment of the present disclosure.
Figure 21:
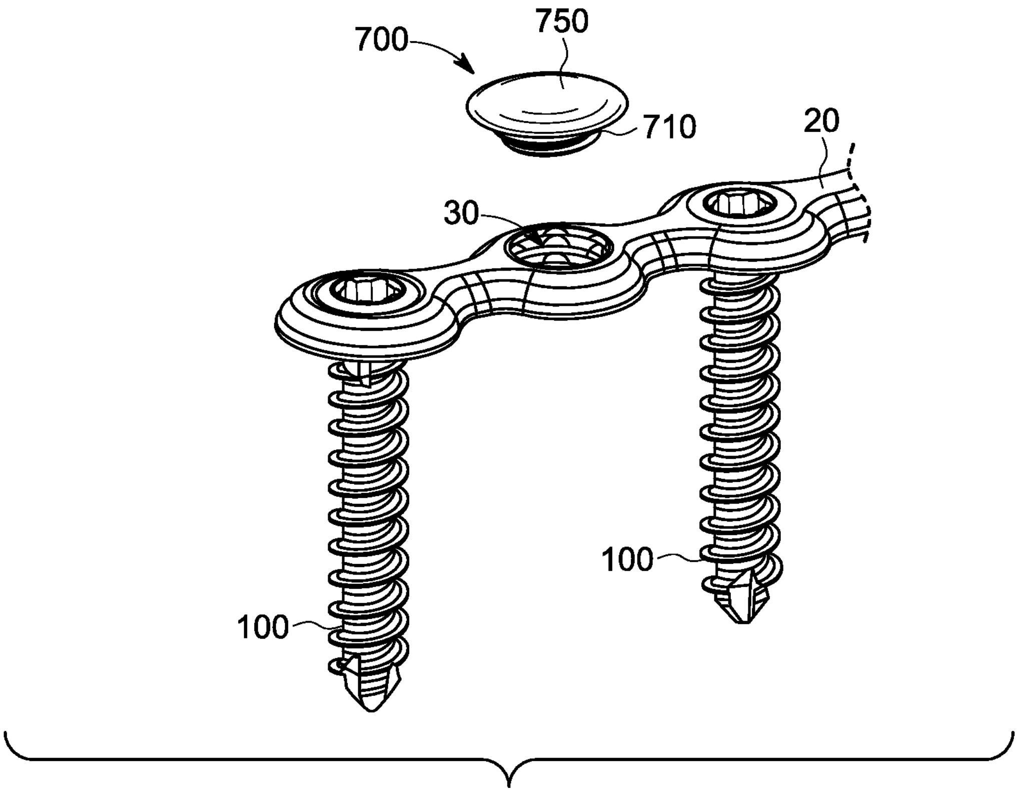
FIG. 21 is an exploded perspective view of the bone plate system of FIG. 20, according to an embodiment of the present disclosure.
Figure 22:
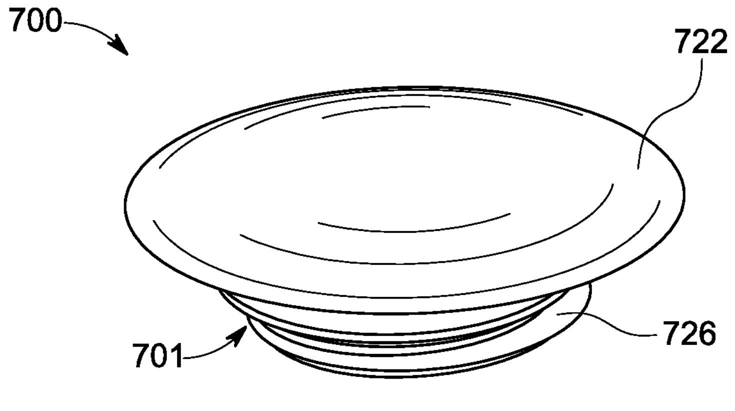
FIG. 22 is an enlarged, top perspective view of the bone plate hole cap of FIG. 20, according to an embodiment of the present disclosure.
Figure 23:
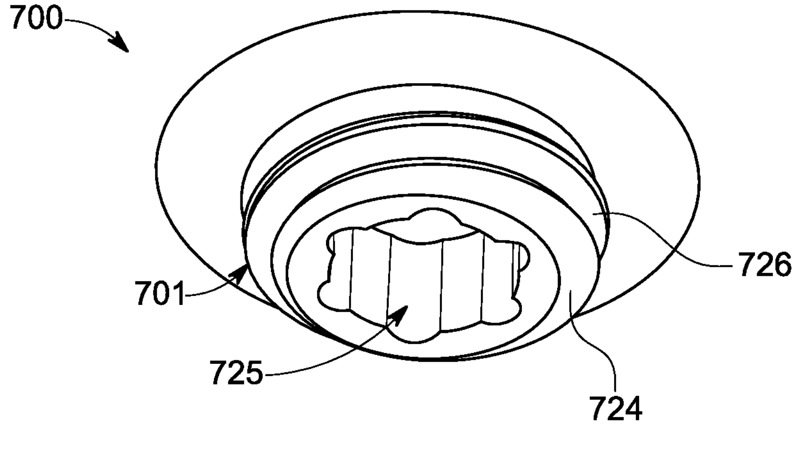
FIG. 23 is a bottom perspective view of the bone plate hole cap of FIG. 22, according to an embodiment of the present disclosure.
Figure 24:
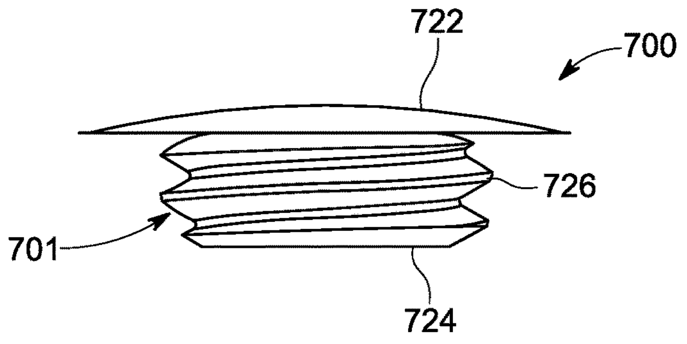
FIG. 24 is a side elevational view of the bone plate hole cap of FIG. 22, according to an embodiment of the present disclosure.
Figure 25:
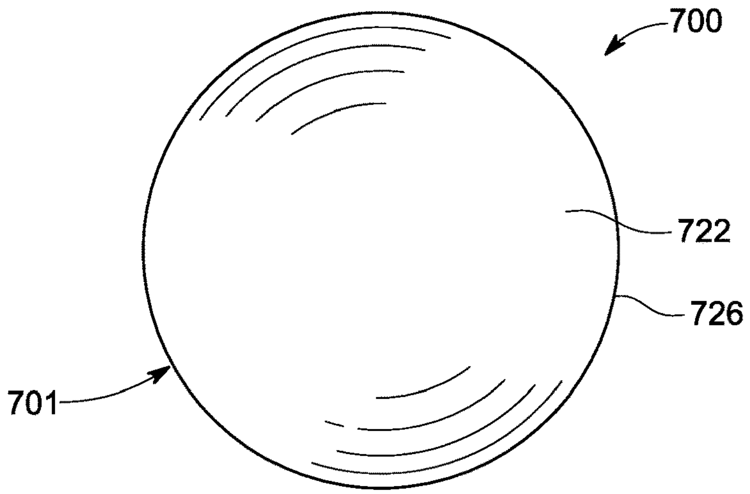
FIG. 25 is a top view of the bone plate hole cap of FIG. 22, according to an embodiment of the present disclosure.
Figure 26:
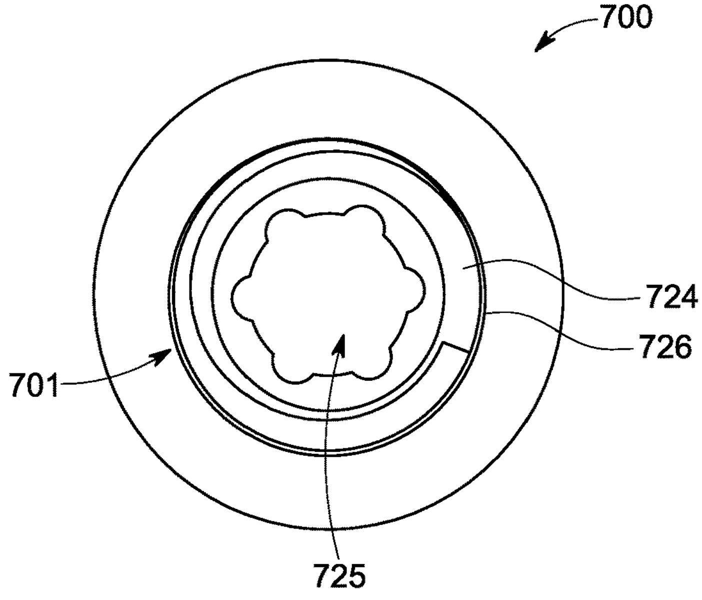
FIG. 26 is a bottom view of the bone plate hole cap of FIG. 22, according to an embodiment of the present disclosure.

FIGS. 20 and 21 illustrate another bone plate system 11, according to an embodiment of the present disclosure. For example, the bone plate system 11 may include a bone plate 20 (only a portion of which is shown), a plurality of fixation elements 100 (only two of which are shown), and at least one bone plate hole cap 700. From the present description, it will be appreciated that the combination of the bone plate 20 with the bone plate hole cap 700 may provide additional strength to the bone plate 20, particularly when a fixation element is not installed in the corresponding through-opening 30 (FIG. 21). In addition, the bone plate hole cap 700 may include a button portion 750 and an attachment portion 710 (FIG. 21). For example, the button portion 750 may be operable to guard against irritation and abrasion from a tendon or other soft tissue that may be progressing/operating over the bone plate hole cap 700.

FIGS. 22-26 illustrate the bone plate hole cap 700, which may include a body 701 having an outwardly-extending first surface 722, a second surface 724, and a peripheral surface 726 disposed between the first surface 722 and the second surface 724 of the bone plate hole cap 700. The peripheral surface 726 may be sized to be restrained or secured in one of the through-openings 30 (FIG. 21) in the bone plate 20 (FIG. 21). For example, the peripheral surface 726 may be sized to mate and engage the through-openings 30 (FIG. 21) in the bone plate 20 (FIG. 21). The peripheral surface 726 may also be a threaded peripheral surface to mate and engage the threaded through-openings 30 (FIG. 21) in the bone plate 20 (FIG. 21). The first surface 722 may be slightly curved such as convex so that first surface 722 extends above a first surface 22 (FIG. 20) of the bone plate 20 (FIG. 20). The bone plate hole cap 700 may include a cavity or recess 725 (FIGS. 23 and 26) extending into the second surface 722 of the body 701 of the bone plate hole cap 700. The cavity or recess 725 (FIGS. 23 and 26) of the body 701 may have, for example, a drive feature for engagement with a tool such as a hex drive for inserting or removing the bone plate hole cap 700 from the bone plate 20 (FIG. 21).

Figure 8:
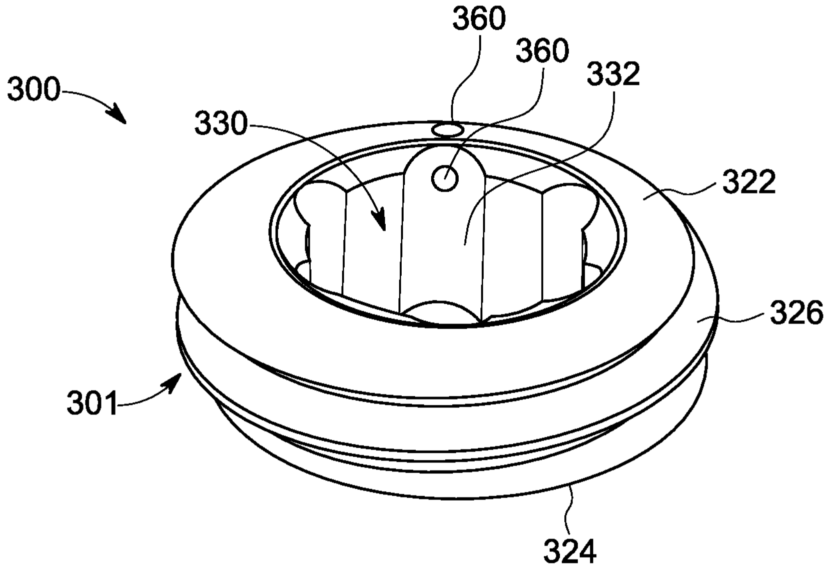
FIG. 8 is an enlarged, top perspective view of the bone plate hole cap of FIG. 1, according to an embodiment of the present disclosure.
Figure 9:
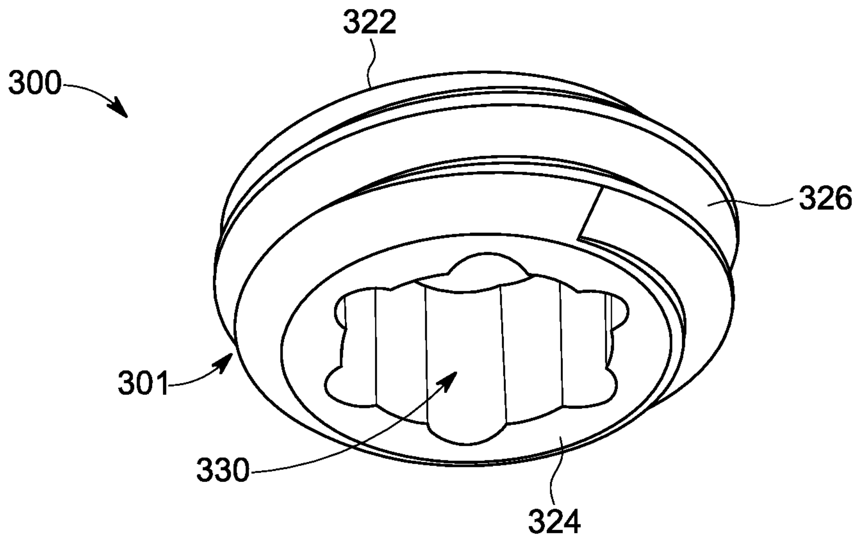
FIG. 9 is an enlarged bottom perspective view of the bone plate hole cap of FIG. 8, according to an embodiment of the present disclosure.
Figure 10:
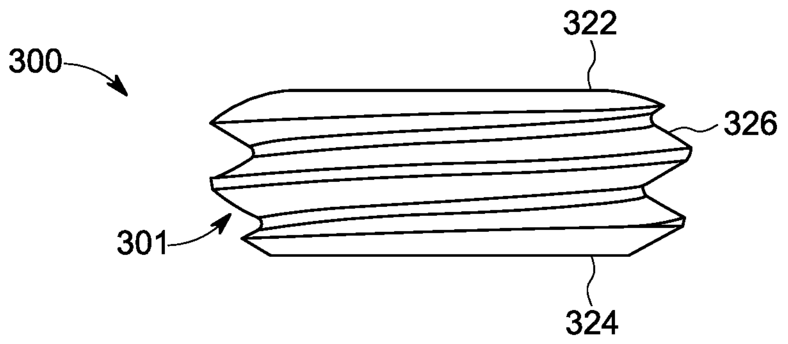
FIG. 10 is an enlarged side elevation view of the bone plate hole cap of FIG. 8, according to an embodiment of the present disclosure.
Figure 11:
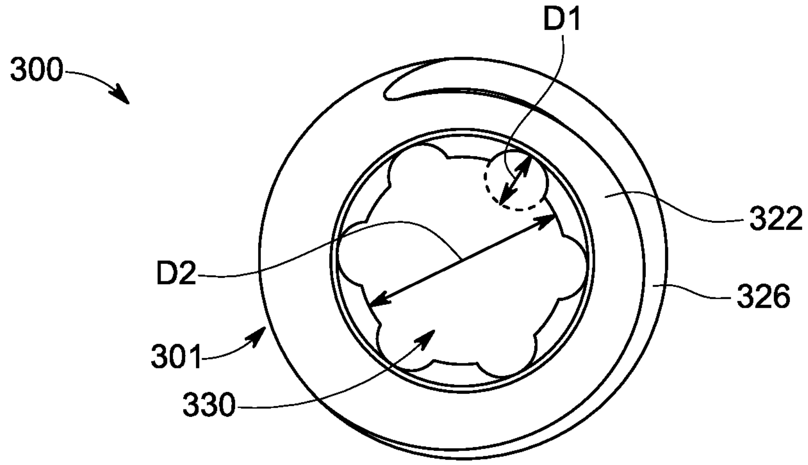
FIG. 11 is a top view of the bone plate hole cap of FIG. 8, according to an embodiment of the present disclosure.
Figure 12:
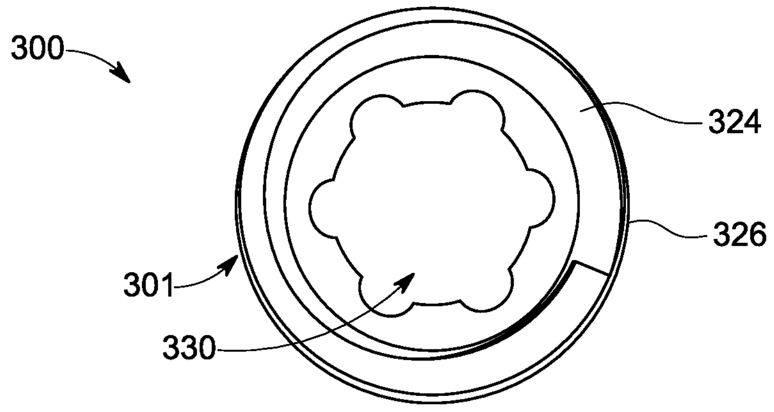
FIG. 12 is a bottom view of the bone plate hole cap of FIG. 8, according to an embodiment of the present disclosure.

In some embodiments, the attachment portion 710 (FIG. 21) may be configured and formed essentially as the same as body 301 (FIG. 8) of bone plate hole cap 300 (FIG. 8). In some embodiments, the button portion 750 (FIG. 21) and the attachment portion 710 (FIG. 21) may be separately formed and attached together.

Figure 27:
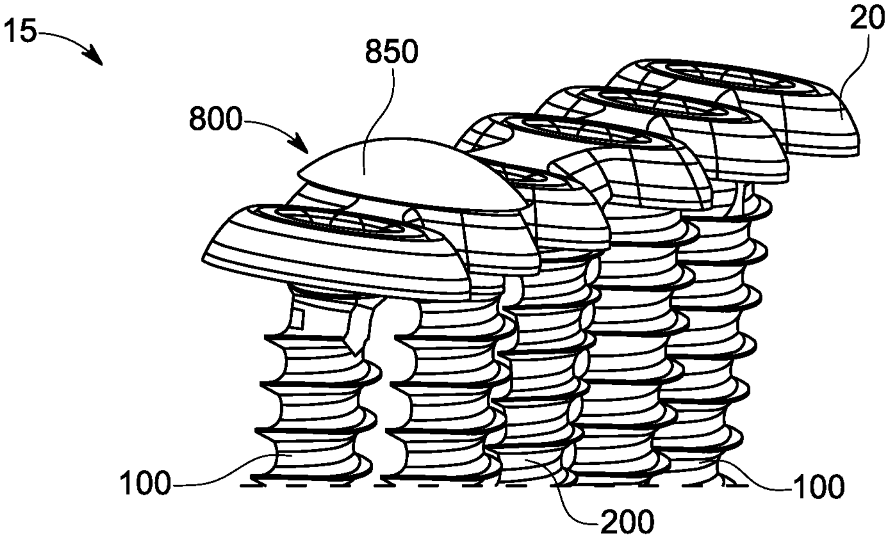
FIG. 27 is a perspective view of another bone plate system, according to an embodiment of the present disclosure.

FIG. 27 illustrates another bone plate system 15, according to another embodiment of the present disclosure. For example, the bone plate system 15 may include a bone plate 20, a plurality of fixation elements 100 and 200, and at least one bone plate hole cap 800. From the present description, it will be appreciated that the combination of the bone plate 20 with the bone plate hole cap 800 may provide additional strength to the bone plate 20, particularly when a fixation element is not installed in the corresponding through hole. In addition, the bone plate hole cap 800 may include a button portion 850 and an attachment portion (not shown in FIG. 27). For example, the button portion 850 may be operable to guard against irritation and abrasion from a tendon or other tissue that may be progressing/operating over the bone plate hole cap 800. In this illustrated embodiment, the bone plate hole cap 800 may be essentially the same as the bone plate hole cap 700 (FIG. 20) with the exception that the button portion 850 of the bone plate hole cap 800 may have a greater or taller profile compared to the button portion 750 (FIG. 20) of bone plate hole cap 700 (FIG. 20). A taller button portion may be operable for tensioning a tendon crossing over the button portion 850 to increase soft tissue stability in that area.

In some embodiments, the attachment portion may be formed from metal such as titanium, stainless steel, cobalt chromium, and the button portion may be formed from a softer material such as a polymer such as PEEK or PE material. In other embodiments, the bone plate hole cap 700 may be a monolithic, integral, and/or of one piece construction formed from a metal such as titanium, stainless steel, cobalt chromium, a polymer such as PEEK, PE, or a composite and/or combination thereof.

Figure 28:
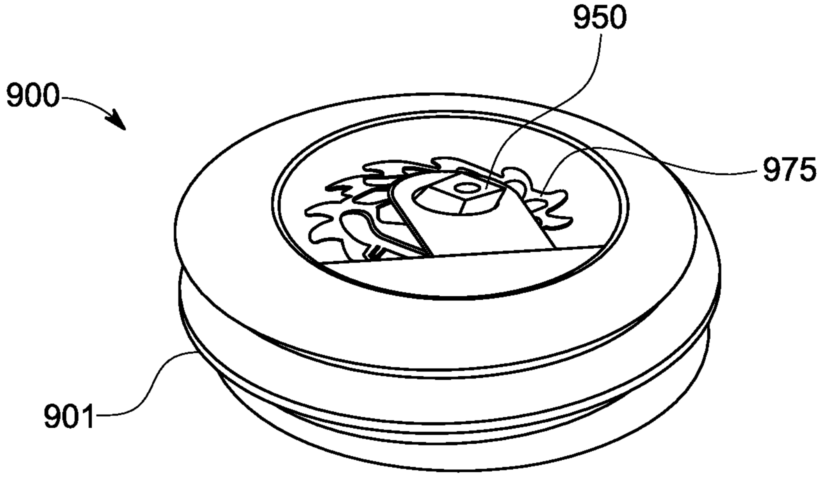
FIG. 28 is a top perspective view of another bone plate hole cap having ratchet mechanism, according to an embodiment of the present disclosure.

FIG. 28 illustrates another embodiment of a bone plate hole cap 900, according to the present disclosure. The bone plate hole cap 900 may be essentially the same as the plurality of bone plate hole caps described above, but with the exception that a body 901 of the bone plate hole cap 900 may include a tensioning or windup feature 950 such as a ratchet mechanism attachable to a suture 975. In some embodiments, a ratchet assembly may be installable in the through-opening or cavity in the body of the bone plate hole cap 900, or integrated into a cover that is installed in the through-opening or cavity in the bone plate hole cap 900.

Figure 29:
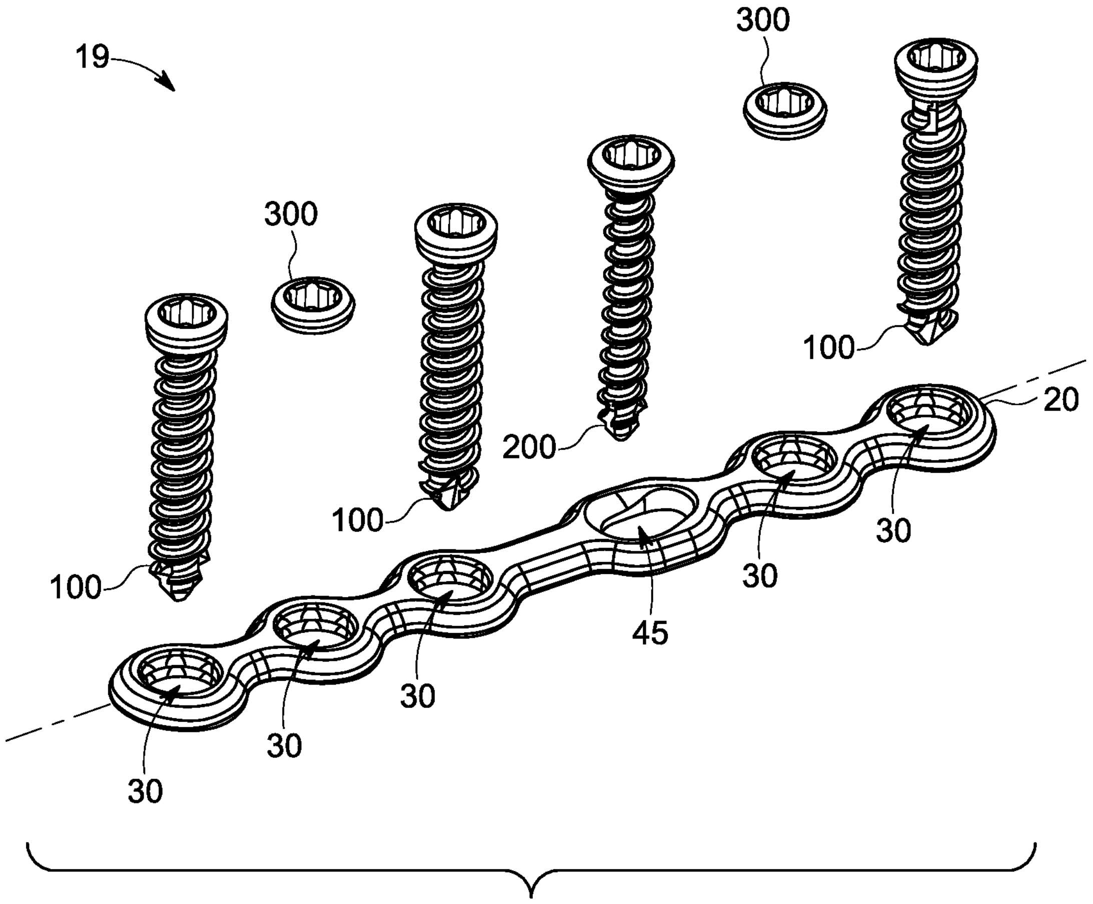
FIG. 29 is an exploded perspective view of another bone plate system, according to an embodiment of the present disclosure.

FIG. 29 illustrates another bone plate system 19, according to an embodiment of the present disclosure. For example, the bone plate system 19 may include a bone plate 20, a plurality of fixation elements 100 and 200, and a plurality of bone plate hole caps 300. From the present description, it will be appreciated that the combination of the bone plate 20 with the bone plate hole cap 300 may provide additional strength to the bone plate 20, particularly when a fixation element is not installed in the corresponding through-opening 30.

From the description herein, it will be appreciated that the various embodiments of the bone plate hole cap may be formed from a metal such as titanium, stainless steel, cobalt chromium, a polymer such as PEEK, PE, or a composite and/or combination thereof.

It will be appreciated that the bone plate hole cap may be operably secured and/or locked in the through-opening in the bone plate employing different attachment means. For example, the bone plate hole cap may be operably secured and/or locked in the through-opening in the bone plate using an interference fit, a cam lock configuration, a key lock configurations or other suitable manner. In some embodiments, the bone plate hole caps may be sized thinner than the bone plate, and may be configured to be secured or locked in the through-opening between the first surface and the bone-engaging surface.

FIG. 30 illustrates a surgical method 1000, according to an embodiment of the present disclosure. The surgical method 1000 using the bone plate systems of the present disclosure may be applicable to achieving bone fixation such as bone fixation within a patient's arm, hand, leg, or foot, and/or preparing a joint for fixation. The method 1000 may include, for example, at 1100 providing a bone plate having a first surface, a second surface, and a plurality of through-openings extending from the first surface to the second surface, at 1200 providing a bone plate hole cap having a first surface, a second surface, and a peripheral surface extending between the first surface and the second surface of the bone plate hole cap, at 1300 selectively securing the bone plate hole cap in one of the plurality of through-openings in the bone plate, at 1400 accessing a bone, at 1500 selectively positioning the bone plate with the bone plate hole cap adjacent to an outer surface of the bone with the bone plate hole cap disposed over a joint line, and at 1600 securing the bone plate to the bone with a plurality of fixation elements extending through some of the other plurality of through-openings in the bone plate, wherein the bone plate with the at least one bone plate hole cap in the one of the plurality of through-openings increases the bending strength of the secured bone plate adjacent to the joint line compared to the secured bone plate adjacent to the joint line without the bone plate hole cap.

The method may further include inserting, for example, temporary fixation pins, olive wires, k-wires or the like to hold the bone plate in position on the distal and proximal bones. The physician may then use fluoroscopy to confirm that the bone plate positioned on the distal and proximal bones in the desired position.

Figure 31:
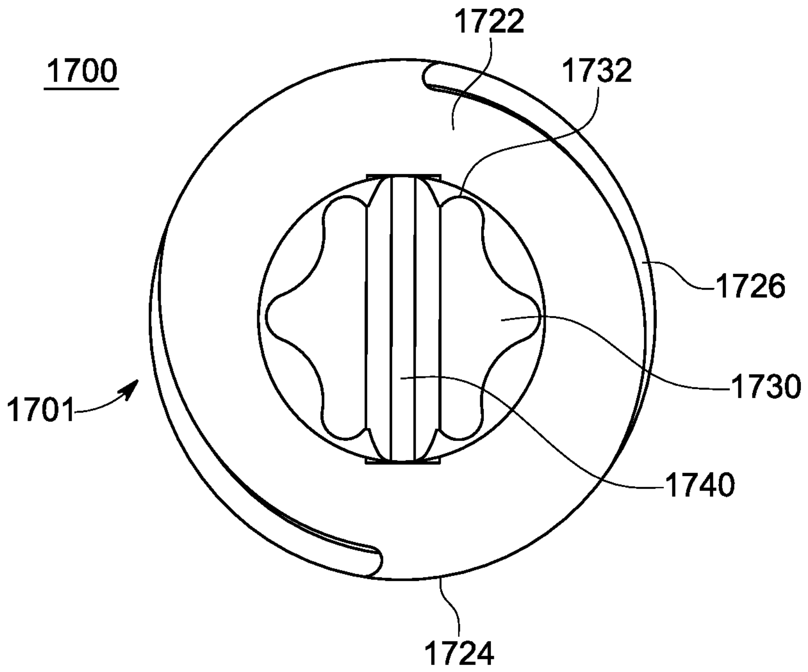
FIG. 31 is an enlarged, top view of another bone plate hole cap, according to an embodiment of the present disclosure.

Referring now to FIG. 31, another bone plate hole cap 1700 is shown, according to one aspect of the present disclosure. The bone plate hole cap 1700 may include a body 1701 having a first surface 1722 and a second surface 1724, an inner surface 1732, and a peripheral surface 1726 disposed between the first surface 1722 and the second surface 1724 and opposite (e.g., on the exterior rather than interior) the inner surface 1732 of the bone plate hole cap 1700. The peripheral surface 1726 may be sized to be restrained or secured in one or more through-openings (e.g., the through openings 30 as shown in the bone plate 20 (FIG. 2). Further, the peripheral surface 1726 may be sized to mate and engage the through-openings 30 in the bone plate 20 (as shown and described with reference to at least FIG. 2). For example, the peripheral surface 1726 may be a threaded peripheral surface to mate and engage the threaded through-openings 30 in the bone plate 20. The bone plate hole cap 1700 may include a through opening 1730 extending along the inner surface 1732 from the first surface 1722 of the body 1701 of the bone plate hole cap 1700 to the second surface 1724 of the body 1701 of the bone plate hole cap 1700. The through opening 1730 of the body 1701 may have, for example, a drive feature for engagement with a tool (e.g., a hex drive, a Torx drive, etc.) for inserting or removing the bone plate hole cap 1700 from the bone plate 20 (FIG. 2). For example, with reference to FIG. 11, the bone plate hole cap 1700 may be formed from a solid blank disk. The through opening 1730 in body 1701 may be formed by drilling six holes having a diameter D1, and then drilling a hole in the center of the disk having a diameter D2.

The bone plate hole cap 1700 is further shown to include a crossing member 1740. The crossing member 1740 is shown to extend diametrically across the through opening 1730 from a first portion of the inner surface 1732 to a second portion of the inner surface 1732 that is substantially opposite the through opening 1730 from the first portion. A suture and/or suture tape (such as those described previously herein) may be threaded in an inferior direction relative to the crossing member 1740, passed beneath the crossing member 1740 within the through opening 1730, and then subsequently threaded in a superior direction relative to the crossing member 1740 such that the bone plate hole cap 1700 is releasably coupled with the bone plate hole cap (e.g., threaded). The crossing member 1740 is shown to be positioned flush with (or slightly offset in the superior or inferior direction) the first surface 1722 of the bone plate hole cap 1700.

It is contemplated that in some embodiments, the bone plate hole cap 1700 may include multiple crossing members the same as and/or similar to the crossing member 1740 disposed adjacent and/or across the through opening 1730 (e.g., perpendicular to one another, spaced at various intervals such as every 60 degrees, spaced inconsistently about the inner surface 1732 of the through opening 1730. The crossing member 1740 may also be configured to have one or more protrusions extending therefrom (some of which may terminate in contact with the inner surface 1732 or within/adjacent the opening 1730) at oblique or orthogonal angles relative to the crossing member 1740. In some embodiments, the crossing member 1740 may be positioned such that traditional drive instruments (e.g., hex, Torx, etc.) may be implemented to manipulate the bone plate hole cap 1700. In some embodiments, instruments with drive features that accommodate the specific geometry of the crossing member 1740 and the bone plate hole cap 1700 may be provided as a portion of a surgical kit. As shown in FIG. 31, the crossing member 1740 is shown to have a substantially cylindrical geometry with a flat arranged on a superior portion of the crossing member 1740. In some embodiments, the crossing member 1740 may include one or more flats arranged about a substantially cylindrical geometry. Further, the crossing member 1740 may also have alternate geometries in some embodiments (e.g., hexagonal, octagonal, symmetrical geometries, asymmetrical geometries, etc.).

In some embodiments, the crossing member 1740 may be integral with the inner surface 1732 of the body 1701 of the bone plate hole cap 1700. Further, in some embodiments, the crossing member 1740 may be coupled with the inner surface 1732 of the body 1701 of the bone plate hole cap 1700. The crossing member 1740 may also have a dynamic configuration, as opposed to the static configuration shown in FIG. 31. For example, the crossing member 1740 may be configured to rotate about a longitudinal axis thereof while remaining fixed and/or coupled with one or more portions of the inner surface 1732 of the body 1701. Such a dynamic configuration may accommodate the threading of a suture underneath/through the crossing member 1740 such that movement of the suture while in contact with the crossing member 1740 drives rotation of the crossing member 1740 about its longitudinal axis.

Figure 32:
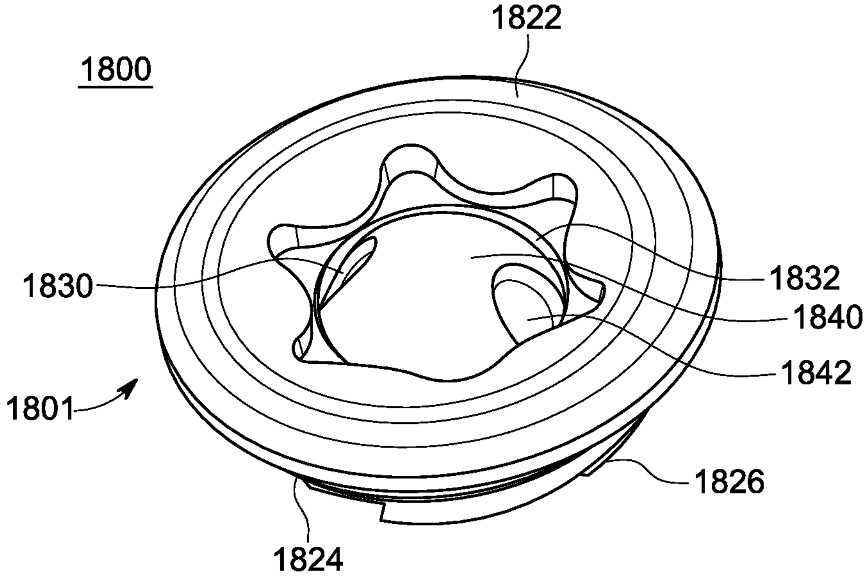
FIG. 32 is an enlarged, top perspective view of another bone plate hole cap, according to an embodiment of the present disclosure.

Referring now to FIG. 32, another bone plate hole cap 1800 is shown, according to one aspect of the present disclosure. The bone plate hole cap 1800 may include a body 1801 having a first surface 1822 and a second surface 1824, an inner surface 1832, and a peripheral surface 1826 disposed between the first surface 1822 and the second surface 1824 and opposite (e.g., on the exterior rather than interior) the inner surface 1832 of the bone plate hole cap 1800. The peripheral surface 1826 may be sized to be restrained or secured in one or more through-openings (e.g., the through openings 30 as shown in the bone plate 20 (FIG. 2). Further, the peripheral surface 1826 may be sized to mate and engage the through-openings 30 in the bone plate 20 (as shown and described with reference to at least FIG. 2). For example, the peripheral surface 1826 may be a threaded peripheral surface to mate and engage the threaded through-openings 30 in the bone plate 20. The bone plate hole cap 1800 may include a through opening 1830 extending along the inner surface 1832 from the first surface 1822 of the body 1801 of the bone plate hole cap 1800 to the second surface 1824 of the body 1801 of the bone plate hole cap 1800. The through opening 1830 of the body 1801 may have, for example, a drive feature for engagement with a tool (e.g., a hex drive, a Torx drive, etc.) for inserting or removing the bone plate hole cap 1800 from the bone plate 20 (FIG. 2). For example, with reference to FIG. 11, the bone plate hole cap 1800 may be formed from a solid blank disk. The through opening 1830 in body 1801 may be formed by drilling six holes having a diameter D1, and then drilling a hole in the center of the disk having a diameter D2.

The bone plate hole cap 1800 is further shown to include a pivot member 1840. As shown in FIG. 32, the pivot member 1840 has a substantially hemispherical or arcuate geometry extending in a superior direction from the through opening 1830. In some embodiments, the pivot member 1840 may have a substantially spherical or arcuate geometry with a portion of said geometry disposed within the through opening 1830. In alternate embodiments, the pivot member 1840 may have one or more geometries other than those shown and described herein. In some embodiments, the bone plate hole cap 1800 may have one or more access points or openings arranged on the peripheral surface 1826 of the bone plate hole cap 1800 so as to facilitate access to and manipulation of the pivot member 1840 (e.g., for positioning, threading of a suture, etc.). The pivot member 1840 is shown to be positioned within and occupy a majority of the through opening 1830. The pivot member 1840 may be releasably, rotatably, and/or pivotably coupled with the inner surface 1832 of the body 1801 of the bone plate hole cap 1800 such that the pivot member 1840 may move (e.g., is capable of pivoting, rotation, etc.) independently of the body 1801 of the bone plate hole cap 1800. The pivot member 1840 is further shown to include a bore 1842 extending from a first portion of an outer surface to a second portion of the outer surface of the pivot member 1840 so as to establish fluid communication therethrough. As shown in FIG. 32, the bore 1842 extends substantially tangentially through the pivot member 1840 (e.g., not diametrically) but in alternate embodiments may have other configurations relative to the pivot member 1840 (e.g., diametrically, along a linear or non-linear, symmetrical, or asymmetrical path). The bore 1842 is configured such that a suture or suture tape such as those shown and described previously herein may be threaded (e.g., received, passed through, etc.) into the bore 1842 so as to releasably couple the bone plate hole cap 1800 with said suture. Upon threading/coupling, the pivot member 1840 enables free rotation of the bone plate hole cap 1800 relative to the threaded suture. Such free rotation may facilitate implantation, for example engaging one or more threads of the bone plate hole cap 1800 with a complimentary threading of a bone plate such as that of those shown and described previously herein. In some embodiments, the pivot member 1840 may be configured such that a suture may be passed through an outer surface of the pivot opening and threaded through the through opening 1830 in an inferior direction such that the suture is arranged adjacent a bone of a patient and/or a bone plate. The pivot member 1840 may be positioned flush with (or slightly offset in the superior or inferior direction) the first surface 1822 of the bone plate hole cap 1800. In some embodiments, a majority of the pivot member 1840 may be enclosed within the through opening 1830 such that free rotation of the pivot member 1840 is permitted within the through opening 1830 (which may serve as a socket or other similar retention space/cavity). In some embodiments, the pivot member 1840 may be positioned such that traditional drive instruments (e.g., hex, Torx, etc.) may be implemented to manipulate the bone plate hole cap 1800. In some embodiments, instruments with drive features that accommodate the specific geometry of the pivot member 1840 and the bone plate hole cap 1800 may be provided as a portion of a surgical kit.

Figure 33:
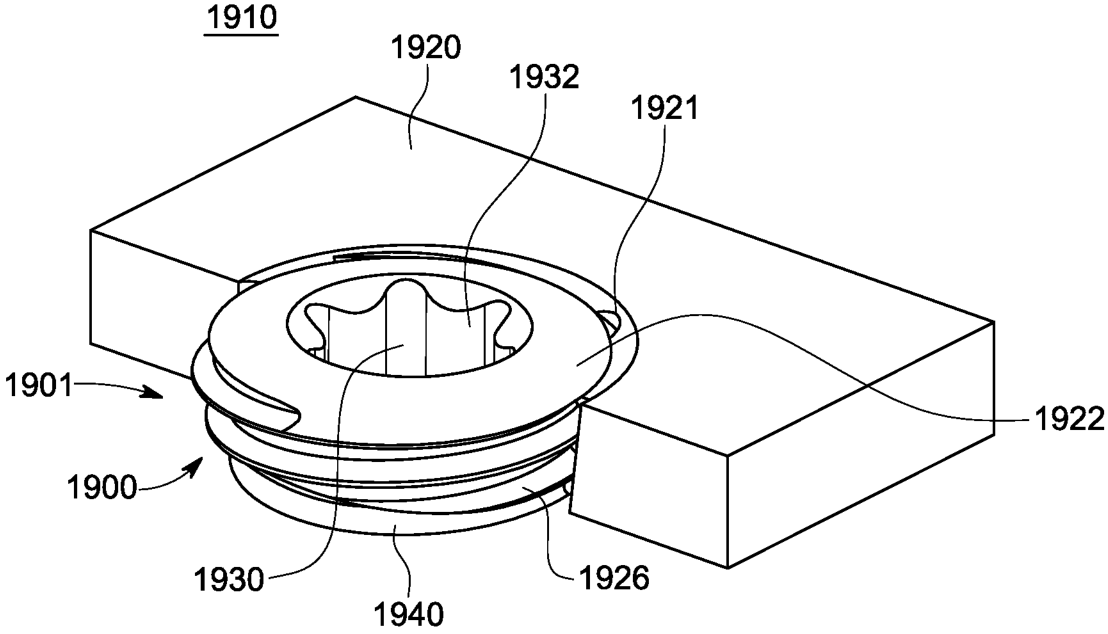
FIG. 33 is an enlarged, top perspective view of another bone plate system, according to an embodiment of the present disclosure.
Figure 34:
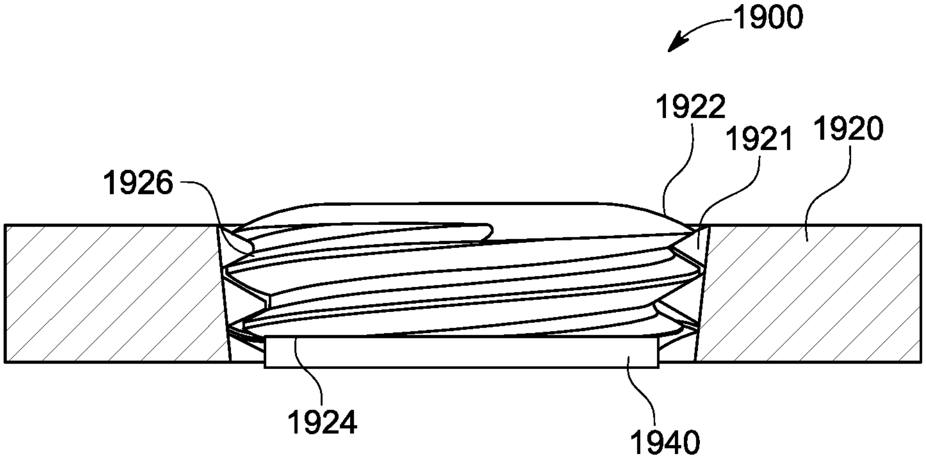
FIG. 34 is a side sectional view of the bone plate system of FIG. 33, according to an embodiment of the present disclosure.

Referring now to FIGS. 33-34, a bone plate system 1910 including a bone plate 1920 and another bone plate hole cap 1900, according to one aspect of the present disclosure is shown. The bone plate hole cap 1900 may include a body 1901 having a first surface 1922 and a second surface 1924, an inner surface 1932, and a peripheral surface 1926 disposed between the first surface 1922 and the second surface 1924 and opposite (e.g., on the exterior rather than interior) the inner surface 1932 of the bone plate hole cap 1900. The peripheral surface 1926 may be sized to be restrained or secured in one or more through-openings (e.g., the through openings 30 as shown in the bone plate 20 (FIG. 2). Further, the peripheral surface 1926 may be sized to mate and engage the through-openings 30 in the bone plate 20 (as shown and described with reference to at least FIG. 2). For example, the peripheral surface 1926 may be a threaded peripheral surface to mate and engage the threaded through-openings 30 in the bone plate 20. The bone plate hole cap 1900 may include a through opening 1930 extending along the inner surface 1932 from the first surface 1922 of the body 1901 of the bone plate hole cap 1900 to the second surface 1924 of the body 1901 of the bone plate hole cap 1900. The through opening 1930 of the body 1901 may have, for example, a drive feature for engagement with a tool (e.g., a hex drive, a Torx drive, etc.) for inserting or removing the bone plate hole cap 1900 from the bone plate 20 (FIG. 2). For example, with reference to FIG. 11, the bone plate hole cap 1900 may be formed from a solid blank disk. The through opening 1930 in body 1901 may be formed by drilling six holes having a diameter D1, and then drilling a hole in the center of the disk having a diameter D2.

The bone plate hole cap 1900 is shown to be releasably coupled with the bone plate 1920, which may be the same as and/or similar to that of the bone plate 20 and/or other bone plates shown and described herein. The peripheral surface 1926 of the bone plate hole cap 1900 is shown to include a thread arranged circumferentially about the peripheral surface 1926, with said thread engaging with a complimentary thread 1921 arranged within a complimentary opening of the bone plate 1920. The bone plate system 1900 is further shown to include a resilient member 1940 arranged inferior relative to the bone plate hole cap 1900. In some embodiments, the resilient member 1940 may consist of nitinol or other materials known to have shape memory properties. The resilient member 1940 may be coupled (releasably or otherwise) with the bone plate hole cap 1900 (e.g., the second surface 1924) and/or a portion of the bone plate 1920. Further, the resilient member 1940 may also be configured to have a press-fit configuration. In some embodiments, the resilient member 1940 may include a threading and/or other engagement feature(s) configured to facilitate engagement and/or coupling with the bone plate hole cap 1900 and/or the bone plate 1920. The resilient member 1940 is shown to have a substantially cylindrical geometry, and in some embodiments such as that of FIGS. 33-34 may have a lateral dimension that is greater than a vertical dimension. In some embodiments, the resilient member 1940 may include a through opening that has the same or similar geometry and dimensions to those of the through opening 1930 of the bone plate hole cap 1900. The resilient member 1940 may be positioned flush with (or slightly offset in the superior or inferior direction) the second surface 1924 of the bone plate hole cap 1900. In some embodiments, the resilient member 1940 may be positioned such that traditional drive instruments (e.g., hex, Torx, etc.) may be implemented to manipulate (e.g., implant, remove, etc.) the bone plate hole cap 1900. In some embodiments, instruments with drive features that accommodate the specific geometry of the resilient member 1940 and the bone plate hole cap 1900 may be provided as a portion of a surgical kit.

The bone plate hole caps 1700, 1800, 1900 (as well as one or more components of the bone plate system 1910) may be implemented in conjunction with (e.g., may be compatible/have cross-compatibility with) one ore more of the systems and/or components thereof shown and described previously. For example, the bone plate hole caps 1700, 1800, 1900 (or, in some aspects, one or more of the bone plate hole caps 1700, 1800, 1900) may be implemented in conjunction with the bone plate system 10 and/or other similar bone plate systems. For example, the bone plate 20 may be implemented in conjunction with the bone plate hole caps 1700, 1800, 1900 as well as the resilient member 1940 positioned within various through openings 30. Further, the bone plate hole caps 1700, 1800, 1900 may be compatible with various sutures, suture tapes, or other similar components commonly used in surgical procedures and soft tissue securement procedures methods.

From the present description, it will be appreciated that the bone plate hole cap and bone plate systems employing at least one bone plate hole cap may provide the advantage of increasing the strength of a bone plate over a joint line such as in high bending situations, providing a tendon fulcrum or post-implant tensioning means, providing a soft tissue friendly button/cover, and providing an auxiliary means to attach suture/tape for soft tissue adjustments and attachments, e.g., suture anchor that attaches to the bone plate hole. In addition, the technique of the present disclosure of filling or occupying the one or more through-openings in a bone plate may inhibit bone growth into the through-openings that are not used to attach the bone plate to a bone.

As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A bone plate system comprising:

a bone plate comprising a body having a first surface, a bone-engaging surface, and a plurality of through-openings extending from said first surface to said bone-engaging surface, said plurality of through-openings defining an inner surface extending between said first surface to said bone-engaging surface of said bone plate;

at least one bone plate hole cap comprising a body having a first surface, a second surface, and a peripheral surface disposed between said first surface and said second surface of said at least one bone plate hole cap, said at least one bone plate hole cap securable in at least one of said plurality of through-openings in said bone plate;

said first surface and/or said second surface of said bone plate hole cap is configured for receiving a drive tool operable for inserting and/or removing the bone plate hole cap into and/or from the bone plate;

at least one cover attachable to said at least one bone plate hole cap, said at least one cover having a top portion and a lower portion;

wherein when said bone plate hole cap is secured in said at least one of said plurality of through-openings, said second surface of said bone plate hole cap is disposed adjacent to said bone-engaging surface of said bone plate;

wherein the bone plate with the at least one bone plate hole cap secured in the one of the plurality of through-openings increases the bending strength of a portion of said bone plate across said bone plate hole cap compared to said portion of said bone plate without the bone plate hole cap; and wherein said lower portion of said at least one cover is configured to correspond to the drive tool.

2. The bone plate system of claim 1, wherein said first surface and/or said second surface of said bone plate hole cap is configured for receiving a male drive tool operable for inserting and/or removing the bone plate hole cap into and/or from the bone plate.

3. The bone plate system of claim 2, wherein the drive tool comprise a standard drive tool.

4. The bone plate system of claim 2, wherein the drive tool comprise a hex drive.

5. The bone plate system of claim 1, wherein said cover comprises a passageway for receiving a suture.

6. The bone plate system of claim 5, wherein said cover comprises a passageway comprising a hole having a first opening disposed adjacent a first peripheral portion of said cover and a second opening disposed adjacent a second peripheral portion of said cover, and said hole extends completely within said cover from said first opening to said second opening.

7. The bone plate system of claim 1, wherein said top portion of said at least one cover comprises a convex surface.

8. The bone plate system of claim 1, wherein said at least one bone plate hole cap comprises a through-opening extending from said first surface of said bone plate hole cap to said second surface of said bone plate hole cap.

9. The bone plate system of claim 1, wherein some of the plurality of through-openings in the bone plate comprises tapered internal threads, and said peripheral surface of said at least one bone plate hole cap comprises corresponding tapered external threads.

10. The bone plate system of claim 9, wherein said tapered configuration of said at least one bone plate hole cap comprises an angle between 2 degrees and 10 degrees.

11. The bone plate system of claim 10, wherein said tapered configuration of said at least one bone plate hole cap comprises an angle between 4 and 8 degrees.

12. The bone plate system of claim 1, wherein said at least one bone plate hole cap comprises a first thickness between said first surface and said second surface of said bone plate hole cap, said bone plate around said at least one of said plurality of through-openings comprises a second thickness between said first surface and said bone-engaging surface of said bone plate, and wherein said first thickness is the same as said second thickness.

13. The bone plate system of claim 1, wherein said bone plate comprises metal.

14. The bone plate system of claim 1, wherein said bone plate hole cap comprises metal.

15. The bone plate system of claim 1, wherein said bone plate hole cap comprises a polymer material.

16. The bone plate system of claim 1, wherein at least one of the plurality of through-openings in said bone plate comprises a compression opening.

17. The bone plate system of claim 1, wherein said at least one bone plate hole cap comprises a plurality of bone plate hole caps.

18. The bone plate system of claim 1, further comprising a plurality of bone fixation elements, said plurality of bone fixation elements extendable through at least some of said plurality of through-openings in said bone plate for securing said bone plate to a bone of a patient.

19. The bone plate system of claim 1, further comprising a plurality of bone screws, said plurality of bone screws extendable through at least some of said plurality of through-openings in said bone plate for securing said bone plate to bones of a patient.

20. The bone plate system of claim 1, wherein said at least one cover extends completely across said at least one of said plurality of through-openings in said bone plate.

21. The bone plate system of claim 1, wherein said cover is press fit to said at least one bone plate hole cap.

22. A bone plate system comprising:

a bone plate comprising a body having a first surface, a bone-engaging surface, and a plurality of through-openings extending from said first surface to said bone-engaging surface, said plurality of through-openings defining an inner surface extending between said first surface to said bone-engaging surface of said bone plate;

at least one bone plate hole cap comprising a body having a first surface, a second surface, and a peripheral surface disposed between said first surface and said second surface of said at least one bone plate hole cap, said at least one bone plate hole cap securable in at least one of said plurality of through-openings in said bone plate;

said first surface and/or said second surface of said bone plate hole cap is configured for receiving a drive tool operable for inserting and/or removing the bone plate hole cap into and/or from the bone plate;

at least one cover attachable to said at least one bone plate hole cap, said at least one cover having a top portion and a lower portion;

wherein when said bone plate hole cap is secured in said at least one of said plurality of through-openings, said second surface of said bone plate hole cap is disposed adjacent to said bone-engaging surface of said bone plate;

wherein the bone plate with the at least one bone plate hole cap secured in the one of the plurality of through-openings increases the bending strength of a portion of said bone plate across said bone plate hole cap compared to said portion of said bone plate without the bone plate hole cap; and wherein some of the plurality of through-openings in the bone plate comprises tapered internal threads, and said peripheral surface of said at least one bone plate hole cap comprises corresponding tapered external threads.

23. A bone plate system comprising:

a bone plate comprising a body having a first surface, a bone-engaging surface, and a plurality of through-openings extending from said first surface to said bone-engaging surface, said plurality of through-openings defining an inner surface extending between said first surface to said bone-engaging surface of said bone plate;

at least one bone plate hole cap comprising a body having a first surface, a second surface, and a peripheral surface disposed between said first surface and said second surface of said at least one bone plate hole cap, said at least one bone plate hole cap securable in at least one of said plurality of through-openings in said bone plate;

said first surface and/or said second surface of said bone plate hole cap is configured for receiving a drive tool operable for inserting and/or removing the bone plate hole cap into and/or from the bone plate;

at least one cover attachable to said at least one bone plate hole cap, said at least one cover having a top portion and a lower portion;

wherein when said bone plate hole cap is secured in said at least one of said plurality of through-openings, said second surface of said bone plate hole cap is disposed adjacent to said bone-engaging surface of said bone plate;

wherein the bone plate with the at least one bone plate hole cap secured in the one of the plurality of through-openings increases the bending strength of a portion of said bone plate across said bone plate hole cap compared to said portion of said bone plate without the bone plate hole cap; and wherein said at least one bone plate hole cap comprises a first thickness between said first surface and said second surface of said bone plate hole cap, said bone plate around said at least one of said plurality of through-openings comprises a second thickness between said first surface and said bone-engaging surface of said bone plate, and wherein said first thickness is the same as said second thickness.

24. A bone plate system comprising:

a bone plate comprising a body having a first surface, a bone-engaging surface, and a plurality of through-openings extending from said first surface to said bone-engaging surface, said plurality of through-openings defining an inner surface extending between said first surface to said bone-engaging surface of said bone plate;

at least one bone plate hole cap comprising a body having a first surface, a second surface, and a peripheral surface disposed between said first surface and said second surface of said at least one bone plate hole cap, said at least one bone plate hole cap securable in at least one of said plurality of through-openings in said bone plate;

said first surface and/or said second surface of said bone plate hole cap is configured for receiving a drive tool operable for inserting and/or removing the bone plate hole cap into and/or from the bone plate;

at least one cover attachable to said at least one bone plate hole cap, said at least one cover having a top portion and a lower portion;

wherein when said bone plate hole cap is secured in said at least one of said plurality of through-openings, said second surface of said bone plate hole cap is disposed adjacent to said bone-engaging surface of said bone plate;

wherein the bone plate with the at least one bone plate hole cap secured in the one of the plurality of through-openings increases the bending strength of a portion of said bone plate across said bone plate hole cap compared to said portion of said bone plate without the bone plate hole cap; and wherein said at least one cover extends completely across said at least one of said plurality of through-openings in said bone plate.

* * * * *